US006960449B2

(12) United States Patent
Wang et al.

(10) Patent No.: US 6,960,449 B2
(45) Date of Patent: Nov. 1, 2005

(54) CLASS CHARACTERIZATION OF CIRCULATING CANCER CELLS ISOLATED FROM BODY FLUIDS AND METHODS OF USE

(75) Inventors: Zheng-Pin Wang, Ellicott City, MD (US); Paul O. P. Ts'o, Ellicott City, MD (US)

(73) Assignee: Cell Works Diagnostics, Inc., Phoenix, MD (US)

( * ) Notice: Subject to any disclaimer, the term of this patent is extended or adjusted under 35 U.S.C. 154(b) by 93 days.

(21) Appl. No.: 09/501,179

(22) Filed: Feb. 10, 2000

(65) Prior Publication Data

US 2002/0098535 A1 Jul. 25, 2002

Related U.S. Application Data

(60) Provisional application No. 60/159,558, filed on Oct. 15, 1999, and provisional application No. 60/119,460, filed on Feb. 10, 1999.

(51) Int. Cl.[7] ............................ G01N 1/30; G01N 33/49
(52) U.S. Cl. ......................... 435/40.5; 435/371; 436/64
(58) Field of Search ............................... 435/40.5, 371, 435/4, 325; 436/64

(56) References Cited

U.S. PATENT DOCUMENTS

| 5,633,945 A | 5/1997 | Kamentsky | 328/129 |
|---|---|---|---|
| 5,674,694 A | 10/1997 | Ross | 435/7.23 |
| 5,962,237 A | 10/1999 | Ts'o et al. | 435/7.23 |
| 6,025,128 A | 2/2000 | Veltri et al. | 435/6 |
| 6,169,816 B1 | 1/2001 | Ravkin | 382/128 |
| 6,197,523 B1 * | 3/2001 | Rimm et al. | 435/7.1 |

OTHER PUBLICATIONS

LaVia et al (Principles of Pathobiology, 1975, p. 213).*
Maggi et al (Cangro, 1963, vol. 16, pp. 169–188).*
Pavone et al (Clinical Ostetrica E Ginecologica, 1963, vol. 65, pp. 475–480).*
Orkin et al ("Report and Recommendation of the Panel to Assess the NIH Investment in Research on Gene Therapy", NIH, 1995).*
Verma et al (Nature, 1997, vol. 389, pp. 239–242).*
Eck et al (Gene-Based Therapy, In: The Pharmacological Basis of Therapeutics, Goodman and Gilman, Ed.s, 1996, pp. 77–101).*
Leverrier et al, Current Biology, 2001, vol. 11, pp. 195–199.*
Ordonez, American Journal of Surgical Pathology, 1998, vol. 22, pp. 1215–1221.*
Wang, Z.P. et al., "Detection incidence of circulating cancer cells from prostate cancer patients' blood," Abstract No. 4708, from the *American Association of Cancer Research* (*AACR*) *Annual Meeting*, Philadelphia, Pennsylvania (Apr. 10–14, 1999).

Wang, Z. –P. et al., "Identification and Characterization of Circulating Prostate Carcinoma Cells," *Cancer* 88:2787–2795, American Cancer Society (Jun. 15, 2000).

Wang, Z.P. et al., "Indications of living circulating prostatic cancer cells in the prostatic cancer patients' blood," from *International Symposium on Biology of Prostate Growth*, National Institutes of Health, Bethesda, Maryland (Mar. 15–18, 1998).

Wang, Z. –P. et al., "Intravascular growth may occur in the formation of a metastatic tumor," *Conference on New Research Approaches in the Prevention and Cure of Prostate Cancer*, Indian Wells, California, American Association for Cancer Research (Dec. 2–6, 1998).

Polascik, T.J. et al., "Influence of Sextant Prostate Needle Biopsy or Surgery on the Detection and Harvest of Intact Circulating Prostate Cancer Cells," *J. Urology* 162:749–752, American Urological Association, Inc. (Sep. 1999).

Ts'o, P.O.P., "Biomarkers Expression and Characterization of Prostate Cancer Circulating Cells," from *Scientific Poster Reproductions: Sixth Annual Scientific Retreat*, Lake Tahoe, Nevada, Oct. 14–17, 1999, Association for the Cure of Cancer of the Prostate, Santa Monica, California.

Ts'o, P.O.P. et al., "Detection and Characterization of Circulating Prostate Cancer Cells in the Blood of Patients with Prostate Cancer," from *Annual Meeting for the Society of Chinese Bioscientists in America*, Toronto (Jul. 1997).

Chen, K.Y. et al., "Detection of Circulating Cancer Cells from Prostate Cancer Patients' Blood," *The First China Taiwan Cancer Conference*, Haerbing, People's Republic of China (Jan. 8–12, 1999).

Polascik, T.J. et al., "Harvest of Intact Prostate Cancer Cells from Blood: Further Characterization of a New Assay," *J. Urology* 159:Supplement (May 31, 1998), from the *Annual Meeting of the American Urological Association*, San Diego, California, May 30–Jun. 4, 1998.

Coleman, A.W., et al., "Mithramycin– and 4'–6–Diamidino–2–Phenylindole (DAPI)–DNA Staining for Fluorescence Microspectrophotometric Measurement of DNA in Nuclei, Plastids, and Virus Particles," *J. Histochem.& Cytochem.* 29: 959–968 (Aug. 1981).

Cote, R.J., et al., "Association of p27$^{Kip1}$ Levels with Recurrence and Survival in Patients with Stage C Prostate Carcinoma," *J. Nat. Cancer Inst.* 90:916–920 (Jun. 1998).

(Continued)

*Primary Examiner*—Karen A. Canella
(74) *Attorney, Agent, or Firm*—Sterne, Kessler, Goldstein & Fox, P.L.L.C.

(57) ABSTRACT

The present invention relates to the identification and characterization of classes and subclasses of circulating cancer cells, including microtumors from body fluid samples using molecular, cytological, and morphological analyses, and methods for staging patients and measuring the efficacy of medical treatments.

19 Claims, 25 Drawing Sheets

OTHER PUBLICATIONS

Cordon–Cardo, C., et al., "Distinct Altered Patterns of p27$^{KIP1}$ Gene Expression in Benign Prostatic Hyperplasia and Prostastic Carcinoma," *J. Nat. Cancer Inst.* 90:1284–1291 (Sep. 1998).

El–Habashi, A.H., et al.,"DNA Ploidy and Proliferating Cell Nuclear Antigen Image Analysis of Peritoneal and Pleural Effusions," *Acta. Cytol.* 41:636–648 (May–Jun. 1997).

Fernandes, B.J., et al., "DNA Content and Estrogen Receptors in Primary Carcinoma of the Breast," *Can. J. Surg.* 34:349–355 (Aug. 1991).

Fidler, I.J., et al., "Critical Factors in the Biology of Human Cancer Metastasis: Twenty–eighth G.H.A. Clowes Memorial Award Lecture," *Cancer Res.* 50:6130–6138 (Oct. 1990).

Galand, P. and Degraef, C., "Cyclin/PCNA immunostaining as an alternative to tritiated thymidine pulse labelling for making S phase cells in paraffin sections from animal and human tissues," *Cell Tissue Kinet.* 22:383–392 (Sep. 1989).

Gerdes, J., et al., "Production of a Mouse Monoclonal Antibody Reactive with a Human Nuclear Antigen Associated with Cell Proliferation," *Int. J. Cancer.* 31:13–20 (Jan. 1983).

Hall, P.A., et al.,"Proliferating Cell Nuclear Antigen (PCNA) Immunolocalization in Paraffin Sections: An Index of Cell Proliferation with Evidence of Deregulated Expression in Some Neoplasms," *J. Pathol.* 162:285–294 (Dec. 1990).

Herbeuval, R., et al., "Diagnosis of Unusual Blood Cells by Immunofluorescence," *Acta. Cytol.* 9:73–82 (Jan.–Feb. 1965).

Kallakury, B.V.S., et al., "The Prognostic Significance of p34$^{cdc2}$ and Cyclin D1 Protein Expression in Prostate Adenocarcinoma," *Cancer* 80:753–763 (Aug. 1997).

Key, G., et al.,"New Ki–67–Equivalent Murine Monoclonal Antibodies (MIB 1–3) Generated Aganist Bacterially Expressed Parts of the Ki–67 cDNA Containing Three 62 Base Pair Repetitive Elements Encoding for the Ki–67 Epitope," *Lab Invest.* 68:629–636 (Jun. 1993).

Kirkegaard, L.J. et al., "Image Cytometric Measurement of Nuclear Proliferation Markers (MIB–1, PCNA) in Astrocytomas," *Am. J. Clin.* 109:69–74 (Jan. 1998).

Lee, A.K.C., et al., "DNA Ploidy, Proliferation, and Neu–oncogene Protein Overexpression in Breast Carcinoma," *Mod. Pathol.* 5:61–67 (Jan. 1992).

Leong, A.S.–Y. and Milios, J., "Is Immunolocalisation of Proliferating Cell Nuclear Antigen (PCNA) in Parrafin Sections a Valid Index of Cell Proliferation?" *Appl. Immunohistochem.* 1:127–135 (1993).

Makris, A., et al., "Changes in hormone receptors and proliferation markers in tamoxifen treated breast cancer patients and the relationship with response," *Breast Cancer Res. Treat.* 48:11–20 (Mar. 1998).

Nagy, K.P., "A Study of Normal, Atypical and Neoplastic Cells in the White Cell Concentration of the Peripheral Blood," *Acat Cytol.* 9:61–67 (Jan.–Feb. 1965).

Sasano, H., et al., "Immunolocalization of Cyclins D and E and Cyclin Dependent Kinase (cdk) 2 and 4 in Human Breast Carcinoma," *Anticancer Res.* 17:3685–3690 (Sep.–Oct. 1997).

Scambia, G., et al., "Multiple Tumour Marker Assays in Advanced Cervical Cancer: Relationship to Chemotherapy Response and Clinical Outcome," *Eur. J. Cancer* 32A:259–263 (Feb. 1996).

Siitonen, S.M., et al., "Proliferating Cell Nuclear Antigen Immunohistochemistry Using Monoclonal Antibody 19A2 and a New Antigen Retrieval Technique Has Prognostic Impact in Archival Paraffin–Embedded Node–Negative Breast Cancer," *Am. J. Pathol.* 142:1081–1089 (Apr. 1993).

Tsihlias, J., et al., "Loss of Cyclin–dependent Kinase Inhibitor p27$^{Kip1}$ Is a Novel Prognostic Factor in Localized Human Prostate Adenocarcinoma," *Cancer Res.* 58:542–548 (Feb. 1998).

Ts'o P.O.P., et al., "Detection of Intact Prostate Cancer Cells in the Blood of Men with Prostate Cancer," *Urology* 49:811–885 (Jun. 1997).

Vielh, P., "Ki67 Index and S–Phase Fraction in Human Breast Carcinomas," *Am. J. Clin. Pathol.* 94:681–686 (Dec. 1990).

Wingren, S., et al., "Flow cytometric analysis of S–phase fraction in brest carcinomas using gating on cells containing cytokeratin," *Br. J. Cancer* 69:546–549 (Mar. 1994).

Yang, R.M., et al., "Low p27 Expression Predicts Poor Disease–Free Survival in Patients with Prostate Cancer," *J. Urology* 159:941–945 (Mar. 1998).

Idziorek, T., et al., "YOPRO–1 permits cytofluorometic analysis of programmed cell death (apoptosis) without interfering with cell viability," *J. Imm. Meth.* 185:249–258 (1995).

Gorczyca, W., et al., "Analysis of Apoptosis in Solid Tumors by Laser–Scanning Cytometry," *Modern Path.* 11:1052–1058 (1998).

Rahilly, M.A., and Fleming, S., "A Tumor Promoter Induces Alterations in Vinculin and Actin Distribution in Human Renal Epithelium," *J. Path.* 166:283–288 (1992).

* cited by examiner

Cell A CK

Cell A Nucleus

Cell B CK

Cell B Nucleus

Cell B ADRgene

Cell C CK

Cell C Nucleus

Cell D CK

Cell C CHR18

Cell E Nucleus

Cell E PSMA

Cell F CK

Cell F Nucleus

Cell G CK

Cell G Nucleus

Cell H CK

Cell H Nucleus

Cell I CK

Cell I Nucleus

| #Total Count: | 17 | | |
|---|---|---|---|
| Obj# | Area | Density Lum | IOD |
| 4 | 1617 | 1288.630 | 2083715 |
| 5 | 1886 | 1338.963 | 2525285 |
| 6 | 1223 | 880.6623 | 1077050 |
| 7 | 1832 | 1324.938 | 2427286 |
| 8 | 1259 | 1028.612 | 1295023 |
| 9 | 1450 | 1500.625 | 2175907 |
| 11 | 1688 | 1367.434 | 2308228 |
| 13 | 1576 | 1362.875 | 2147891 |
| 14 | 4963 | 912.7314 | 4529886 |
| 15 | 5506 | 949.8057 | 5229630 |
| 17 | 1428 | 1229.701 | 1756013 |
| 18 | 1744 | 1005.263 | 1753178 |
| 19 | 1332 | 1329.164 | 1770446 |
| 20 | 1581 | 954.5616 | 1509162 |
| 21 | 1544 | 1224.475 | 1890589 |
| 22 | 1531 | 1116.885 | 1709951 |
| 24 | 1849 | 905.4127 | 1674108 |

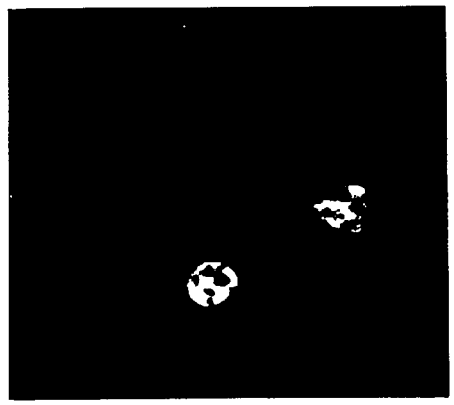 
FIG.9A  FIG.9B
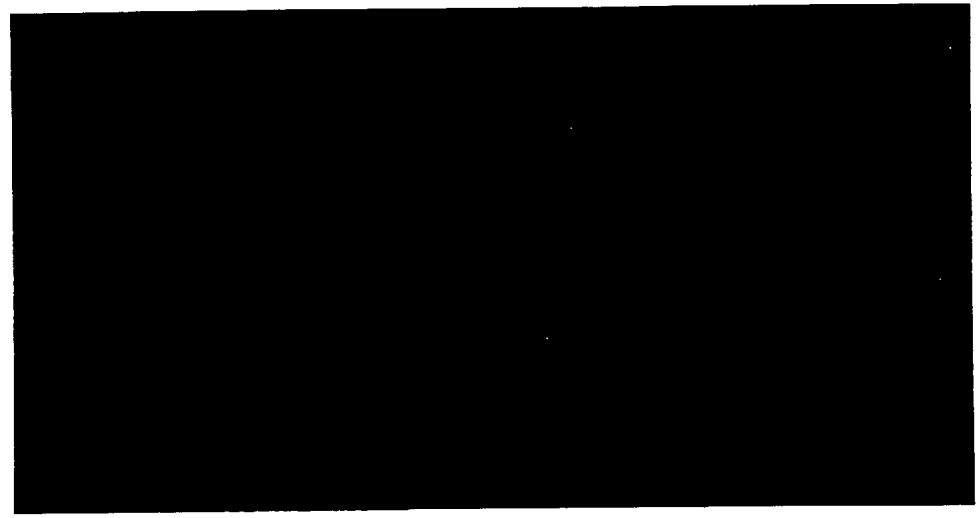
FIG.10

CK and Nucleus

ER

CK and Nucleus

PR

CLASS CHARACTERIZATION OF CIRCULATING CANCER CELLS ISOLATED FROM BODY FLUIDS AND METHODS OF USE

CROSS-REFERENCE TO RELATED APPLICATIONS

This application claims the benefit of U.S. Provisional Application No. 60/119,460, filed Feb. 10, 1999, and U.S. Provisional Application No. 60/159,558, filed Oct. 15, 1999, the contents of each which are fully incorporated by reference herein.

STATEMENT AS TO THE RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention pursuant to Grant No. DOD #980996.

BACKGROUND OF THE INVENTION

1. Field of the Invention

The present invention is directed to the identification and characterization of classes and subclasses of circulating cancer cells, including microtumors, from body fluid samples.

2. Related Art

Metastases are established potentially by cancer cells, derived from a primary or a secondary tumor site, that are released into the circulation via the blood and/or the lymphatic system. Metastatic dissemination can be an early event in the natural history of many malignant epithelial tumors. Blood serves as a passage between the primary and metastatic site that is ultimately seeded by tumor cells that survive detachment and circulation in the peripheral blood and bone marrow. The initial concept for the development of a metastasis and infiltration of blood vessels by cancer cells from a primary malignant tumor was formulated by Cruveilhier in 1829 and confirmed by Ashworth in 1869 (Ashworth, et al, *Aust. Med J.* 14:146 (1869)). Ashworth et al. described cells in the blood resembling those found in malignant skin tumors at autopsy, but the malignant nature of these cells was not determined with certainty.

In the blood circulation, the metastatic pathway can be developed via intravascular or extravascular growth. During the extravascular metatstatic process, the tumor cells undergo a series of sequentially-linked steps. For example, the tumor cells intravasate, survive in the circulation, embolize, arrest in distant capillaries, extravasate, and multiply in organ parenchyma to generate a secondary or tertiary tumor (Fidler, I .J., *Cancer Research* 50:6130–6138 (1990)).

The definitive classification of a malignant cell found in a body fluid sample remains challenging. Many early cancer researchers were cytologists whose identification criteria for cancer cells were established by the Papanocolau method id and Romanowsky stains. Such criteria for classifying a cell as malignant included the following morphological examination: abnormal cell size and shape, a large nucleus with an abnormal chromatin network, prominent (often multiple) nucleoli, scanty cytoplasm, and cytoplasmic vacuolation. Due to a previous lack of specific identification criteria for circulating cancer cells, these cells could not be easily distinguished from blood cell precursors, a typical forms of cells normally found in the blood, or cells foreign to the blood. Multiple staining methods (including fluorescent staining techniques, but without molecular markers) were advocated for the identification of circulating cancer cells (Herbeuval et al, Acta. *Cytol.* 305:73–82 (1965); Nagy et al., Acta. *Cytol.* 305:61–67 (1965)). The advent of monoclonal antibodies, nucleic acid probes, and multiple fluorescent dyes, and the development of multiple filter functions for fluorescence microscopy have aided in the elucidation of circulating cancer cells isolated from patients.

Invasive potential has been linked to chromosome aneuploidy, hormone receptors, cell proliferation markers, and proliferative cell nuclear antigen (PCNA). Chromosome aneuploidy in cancer patients and the relationship to invasiveness in clinical applications have been correlated by Wingren, et al., *Br. J. Cancer* 69: 546–549 (1994). Further, using flow cytometry on cells derived from breast cancer patients, Lee, et al, *Mod. Pathol.* 5: 61–67 (1992), found that aneuploidy was significantly related to the loss of estrogen receptors, high histologic grade, high nuclear grade and mitotic rate. Immunohistochemical evaluation of proliferation by staining with Ki67 monoclonal antibody correlated strongly with mitotic rate. Aneuploid and polyploid tumors demonstrated higher Ki67 scores than diploid tumors. Correlation was demonstrated between aneuploidy and low levels of estrogen receptors (Fernandes, et al., *Can. J. Surg.* 34: 349–355 (1991)).

Invasive potential has been linked with cell proliferation markers, such as MiB1/Ki67 and proliferating cell nuclear antigen (CNA). MiB1/Ki67, introduced by Gerdes, *Int. J. Cancer* 31: 13–20(1983), provides a direct means of evaluating the growth fraction of tumors in histopathology and cytopathology (Key, et al, *Lab. Invest.* 68: 629–636 (1993)). Sasano, et al, *Anticancer Res.* 17:3685–3690 (1997)) found a significant correlation between the cell proliferation MiB1/Ki67 marker and invasive ductal breast carcinoma. Vielh, *Am. J. Clin. Pathol* 94: 681–686 (1990), conducted a study of immunohistologic staining (Ki67 index) versus flow cytometry using a Ki67 monoclonal antibody. Immunohistochemical studies provided better proliferative indices than flow cytometry. PCNA is also a good marker of cell proliferation with evidence of deregulated expression in some neoplasms and occasional upregulation in benign tissue (EL-Habashi, et al., Acta *Cytol.* 41:636–648 (1997); Hall, et al., *J Pathol.* 162:285–294 (1990); Leong and Milios, *Appl. Immunohistochem* 1:127–135 (1993); Siitonen, et al., *Am. J. Pathol.* 142:1081–1088 (1993); Galand and Degraef, *Cell Tissue Kinet.* 22:383–392 (1989)). Kirkegaard, et al., *Astrocytomas. Anat. Pathol.* 109:69–74 (1997), found in astrocytomas that proliferation, measured as MiB1/Ki67 and PCNA by image cytometry, correlated significantly with histologic grade and patient survival.

The P27/Kip proteins play an important role as negative regulators of cell cycle-dependent kinase activity during progression of the cell cycle. Tsihlias, et al., *Cancer Res.* 58:542–548 (1998)) found prostate cancers that had increased P27 staining were correlated with benign prostatic epithelial components in all tumor sections.

Correlation of proliferation markers, estrogen receptors, and drug therapy in circulating cells has been done with breast cancer biopsy material by Makris, et al., *Breast Cancer Res. Treat.* 48:11–20 (1998) in a "first-time" study where an early decrease in proliferation marker was shown to relate to the subsequent clinical response to tamoxifen therapy.

A sensitive test has been developed for enrichment of circulating cancer cells by using double gradient centrifugation and immunomagnetic cell sorting to deplete most erythrocytes and leukocytes (U.S. Pat. No. 5;962,237). Isolated circulating cancer cells are characterized using multiple identification markers, such as epithelial, tissue or cell-specific markers, chromosome aneuploidy markers, and nuclear markers (Ts'o, P. O. P., et al. *Urology* 49(6):881–885 (1997)).

Still, with current techniques and knowledge, the pathway of secondary tumor formation via intravascular growth of tumor cells in the circulation lacks sufficient distinction. Reasons for this general lack of understanding include the complex nature of cancer, the many different kinds of cancer, the lack of suitable technology for detecting and characterizing multistaged circulating tumor cells, and the difficulty of describing the fate of the circulating cancer cells in an intact physiological state. Molecular, cytological, and/or morphological characterization of circulating cancer cells isolated from body fluids, including peripheral blood, is designed to address these concerns and is the subject of this invention.

SUMMARY OF THE INVENTION

The invention relates to characterizing isolated cancer cells from a body fluid sample from an animal such as a mammal, preferably a human. Using fluorescence microscopy, circulating cancer cells are characterized by molecular, cytological, and/or morphological markers to analyze and distinguish cancer cell classes and subclasses, wherein the classes and subclasses comprise a terminal cell, a proliferative cell, or an intermediate cell. It is a preferable embodiment of the invention to determine whether the cancer cell moves along a proliferative pathway or a terminal pathway in its development.

The invention further relates to a method of characterizing circulating cancer cells to assess the health status of an animal such as a mammal and/or to determine whether the cancer is progressing, stable, or is being terminated. Embodiments of the present invention also provide methods for monitoring and staging the cancer and providing cell characterization information to assist with treatment options, including surgery, radiation, and drug treatment. In another embodiment, circulating cancer cells isolated from body fluid samples are monitored for morphological, cytological, and/or molecular changes.

The invention further relates to a method of characterizing cancer cells comprising developing a characterization profile based upon the morphological, cytological, and molecular characteristics of circulating cancer cells isolated from a body fluid.

The invention further relates to a method of determining the presence or absence of metastatic cancer cells, comprising:
  (a) isolating circulating cancer cells in a body fluid sample of a patient with cancer or a patient suspected of having cancer;
  (b) characterizing said isolated cells using cytological and morphological analyses by fluorescence microscopy to distinguish cancer cell classes;
  (c) determining the classification of the cancer cells isolated, wherein the cancer cell classification comprises terminal cells, proliferative cells, and/or intermediate cells; and
  (d) assessing whether metastatic cancer is present or absent based on the classification determined in (c).

The invention further relates to a method of determining the efficacy of a medical procedure, comprising:

(a) conducting a first isolation of circulating cancer cells in a body fluid sample of a patient with cancer or a patient suspected of having cancer;
  (b) characterizing said isolated cells using cytological and morphological analyses by fluorescence microscopy to distinguish cancer cell classes;
  (c) determining the classification of the cancer cells isolated, wherein the cancer cell classification comprises terminal cells, proliferative cells, and/or intermediate cells,
  (d) conducting a second isolation of circulating cancer cells in a body fluid sample of the patient;
  (e) repeating (b) on the cells from the second isolation;
  (f) repeating (c) on the cells from the second isolation; and
  (g) assessing whether a medical procedure is efficient based on the classification determined in (c) as compared to the classification determined in (f).

In one embodiment, the first isolation is conducted before the administration of the medical procedure and the second isolation is conducted after the administration of the medical procedure.

In another embodiment, the presence of more terminal cancer cells in the second isolation than in the first isolation is indicative of a positive response to the medical procedure.

In another embodiment, the presence of more proliferative circulating cancer cells in the second isolation than in the first isolation is indicative of a negative response to the medical procedure.

In another embodiment, an increase or no change in the level of circulating cancer cells during or after terminating the medical procedure for a period of time is indicative of a negative response to the medical procedure.

The medical procedure is selected from the group consisting of surgery, radiation, hormone therapy, gene therapy, and therapeutic agent(s) administration, and a combination thereof.

BRIEF DESCRIPTION OF THE FIGURES

FIGS. 1A–1I represent a general schematic which depicts terminal and proliferative pathways of cancer cells as defined by specific molecular, cytological, and morphological characteristics.

FIGS. 9A and 9B are monochromatic images of dying breast cancer cells.

FIG. 10 is a monochromatic image of an LnCap cell.

FIG. 12A depicts cytokeratin staining and FIG. 12B depicts DAPI staining.

FIG. 13A depicts cytokeratin staining and FIG. 13B depicts DAPI staining.

DETAILED DESCRIPTION OF THE PREFERRED EMBODIMENTS

Figure 1:
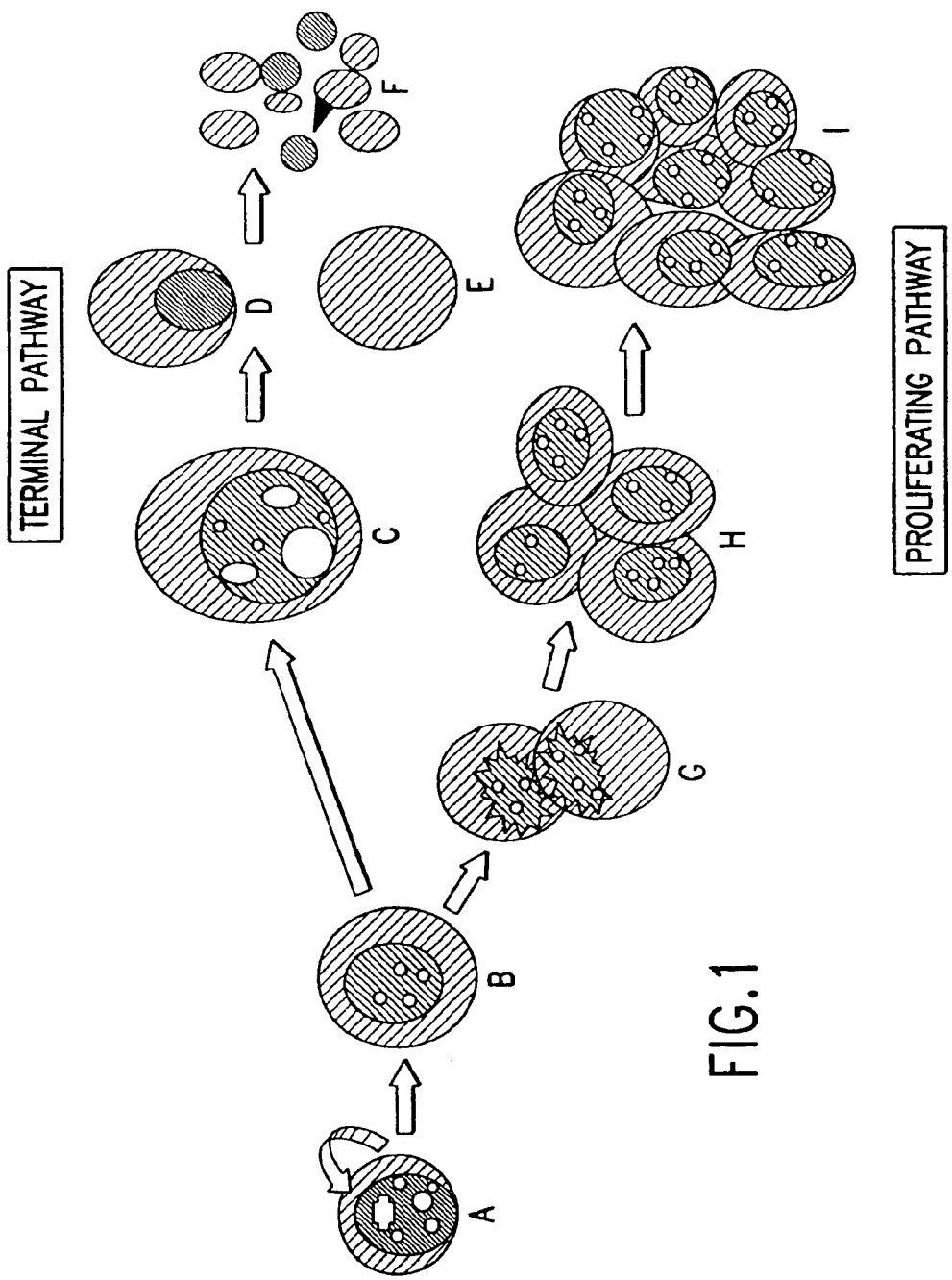
FIGS. 1A–1I are schematics of the cytological progression of cancer cell types of the dynamic neoplastic developmental pathway.

The present invention relates to the identification and characterization of classes and subclasses of isolated cancer cells in a body fluid sample based upon cytological analyses using fluorescence microscopy. In a preferred embodiment of the invention, the cancer cells are circulating cancer cells; and more preferably, the circulating cancer cells are epithelial in origin. The occurrence of circulating epithelial cells in a blood or bone marrow sample is a strong indication of the presence of metatstatic cancer since epithelial cells are normally not found circulating in the blood. A more significant indication of metastases is to characterize cells as "viable" with the potential of forming microtumors. While not wishing to be bound to any particular theory, it has been postulated that blood borne malignant cells must be viable and possess the potential to proliferate in order to establish metastatic growth while lodged in other organs in the body or in the circulation or bone marrow. Characterization of an isolated cancer cell from a body fluid sample may capture the stage of its development showing that its evolving by neoplastic progression in a "proliferative" pathway or that it is a dying cell destined for death in a "terminal" pathway.

There are different approaches that may be taken to characterize cancer cells. The approaches can be taken individually or combined. "Cytological" approaches of characterization refer to the origin, structure, including morphology, function, including biochemical, biology, molecular biology, and pathology of cells. A preferred cytological approach is based on "exfoliative cytology" which relates to the microscopic examination of cells, especially epithelial cells, desquamated from a body surface, such as an organ, as a means of detecting malignant change.

"Molecular" biological approaches to characterization refer to the identification of biological phenomena at the molecular level through the study of DNA and RNA, proteins, and other large molecules involved in genetic information and cell function, and more particularly, to a "molecular disease" as it relates to a change in a protein molecule that may be a result of an allelic alteration, including over-expression, under-expression, or non-expression of a single gene or multiple genes. "Morphological" approaches to characterization of a cell mean the physical appearance of a cell and its components. Such characterization may include cellular and nuclear attributes, such as size and shape, aneuploidy status, cellular and nuclear staining, including various cytological and E molecular marker staining, such as cell origin, e.g., epithelial, and organ type, e.g., prostate, breast, etc., and any measurement of a normal or abnormal biological marker.

In particular, a characterization profile of the expression of markers of a cancer cell may delineate normal or abnormal measurements at the biological and molecular levels (such as DNA or RNA with variations or mutations, such as p53), and at the gene expression level (such as mRNA or protein), and more preferably the over- or under-expression of DNA, RNA, and/or protein can be compiled for an assessment of the staging of the cancer cells in a body fluid sample.

Molecular, cytological, and morphological analyses comprise a collection of factors to distinguish cancer cell classes and subclasses, which includes, but is not limited to, evaluating the shape of the cell and measuring its diameter, recording the gradient cell density at which the cells were isolated, determining the presence or absence of a nucleus, the shape of the nucleus, the dividing or resting state of the cell, whether there is a cluster of 3 or more cells, and the cell type. Cell type may be identified using cell-specific markers for the identification of epithelial cells, for example, or tissue or organ-specific markers that identify prostate, breast, pancreas, ovarian, bladder, liver, ovary, rectum, kidney, colon, gastric, lung, and the like. Specific molecular or biochemical markers including apoptotic, enzymatic such as thymidylate synthetase, and/or oncogenic such as p53, chromosome number, and any other state-of-the art protein, DNA, and RNA markers that are clinically relevant.

A preferred embodiment of the invention concerns the characterization of classes and subclasses of isolated cancer cells in blood samples that may be useful for screening, diagnosing, assessing, and monitoring cancer patients, patients suspected of having cancer or patients at risk for cancer. For example, molecular, morphologic, and cytologic analyses of prostate and breast cancer cells isolated from peripheral blood suggest a classification scheme based on three primary categories: terminal cells, proliferative cells, and intermediate cells.

Thus, the neoplastic developmental pathway may contain a mixture of cancer cell types. One such cell type is a stem cell-like cancer cell that appears as an undifferentiated cell. This cell has a relatively small cell body, exhibits aneuploidy, has a well developed cytokeratin network, and is considered a "dense cell," e.g., a cellular density for collection in an about 1.077 g/ml or higher density gradient medium (FIG. 1A). These "growing" or "stem cell-like" cancer cells have a diameter of about 12 to 20 micrometers and in general, contain a nucleus that is elliptical or round in shape. In addition, these stem cell-like cells are characterized as "young," "immature," and/or undifferentiated with rough and granular chromatin and they have a high nuclear to cytoplasm ratio, wherein the nucleus is a large oval-shaped nucleus with scant cytoplasm (based on DAPI staining). This cell most closely resembles a normal, non-cancerous cell, although the cell is a neoplastic cell as its ploidy status, e.g., polyploid, deviates from a cell's normal genetic status. These cells stain positive for cytokeratin and exhibit a less structured network than the indeterminate cell as shown in FIG. 1B, described below. If these cells are prostate cells, strong homogeneous PSMA expression is exhibited when stained with anti-PSMA antibodies with intense staining exhibited at the edges.

Most of the stem cell-like cancer cells are found to be in interphase or a resting phase. Interphase is the interval between two successive cell divisions, during which the chromosomes are not individually distinguishable and the normal physiological processes proceed. These stem cell-like cells appear to proceed a distinct cell type-identifiedas "indeterminate" or "intermediate." Stem cell-like cancer cells may remain in a replication mode to generate additional stem-cell like cancer cells or they may advance to a neoplastic progression mode which is a progressive process in neoplastic transformation involving a cell type depicted by FIG. 1B. In essence, the cell type of FIG. 1A advances to a cell type depicted by FIG. 1B wherein, the cells may develop along the proliferative pathway, depicted by FIGS. 1G, 1H, and 1I, or be instructed to follow the terminal pathway depicted by FIGS. 1C, 1D, 1E, and 1F, described below. Thus, FIG. 1B may progress to any one of the terminal cell types depicted in FIG. 1. In some cases, the indeterminate cell may eventually progress through to the final terminal cell type, denoted as FIG. 1F, or the terminal cell may be eliminated at any step in the terminal pathway by scavenger cells.

As noted above, a descriptive profile of cytological characteristics of cancer cells may provide insight regarding the nature of the cancer. Specifically, the cytological characteristics may allow for the classification of the cancer cells into three major classes, terminal, proliferative, and indeterminate which are described in more detail below.

The Terminal Pathway

Terminal cancer cells comprise several different cell types based upon cytological characteristics. Characteristics of terminal cells are growth arrested, and/or are undergoing or have undergone apoptosis and/or necrosis. Thus, terminal cells are expected to die and be eliminated from the body. All epithelial cancer cells assessed as terminal cells are cytokeratin positive, including the cell fragments found in FIG. 1F.

FIG. 1B depicts an intermediate cell type which can be a cell type of the terminal pathway. The cells are elliptical or round with a diameter of about 20 to about 30 micrometers. These cells contain a large nucleus with more cytoplasm than the stem cell-like cells.

FIG. 1C depicts a terminal cancer cell type which comprises a cell that is very large in size in comparison with white blood cells (WBCs) from the same patient. In particular, these cells have a diameter of about 20 to about 50 micrometers, and more specifically, about 30 to about 50 micrometers. These cells may be elliptical, round, or irregular and possess a nucleus (as determined by DAPI staining). The nuclei are very large and loose in structure as determined by DAPI staining, wherein the loss of nuclear chromatin pattern is beginning to occur. Further preliminary analyses with DAPI shows that the nuclei usually have an irregular shape and generally have 2 to 3 times more DNA than WBCs (based on DNA quantitation studies). The internal integrity of this cell type appears to be compromised. These cells are light in density, fragile, and are captured in an about 1.068 g/ml density gradient medium. Their fragility prohibits this cell type from withstanding complex isolation procedures, which includes the use of magnetic beads. The nucleus appears to expand with the cell and results in a high nucleus to cytoplasm ratio when compared to a WBC from the same patient. Large vacuole-like images appear within the nucleus.

FIGS. 1D and 1E depict cells that are round or irregular in appearance. The diameter of these cell types is about 20 to 30 micrometers. The cells depicted in FIG. 1D contains nuclear material that becomes very dense, wherein the nuclear material appears with pyknotic degeneration and condensed homogeneous chromatin. These cells have a typical network structure based upon cytokeratin staining and are also positive for apoptotic markers, e.g., as determined by TUNEL staining. The cells depicted in FIG. 1E are enucleated (contain no nucleus as determined by DAPI staining) as the cells undergo nuclear and cytoplasmic degeneration. Without wishing to be bound to any particular theory, one explanation suggests that the nuclear content of the cell is leaked into the cytoplasm. Another explanation suggests that the DNA is ejected from the cell. The cells develop an irregular shape and maintain a typical network structure as shown by positive cytokeratin staining. These cells are about 20 to about 40 micrometers in diameter, and more specifically, about 20 to about 30 micrometers If these cells are prostate cells, they stain positively for PSMA antibodies. Cells can be measured using a Vernier glass slide with a calibrated ruler (Zeiss, West Germany) or any other cell measuring device known to those of ordinary skill in the art.

Another cell type of the terminal pathway of cancer cells, shown in FIG. IF, comprises cells that break apart into pieces. Although these cells can be classified as developing an irregular shape, it is not particularly advantageous to measure the diameter of these cells. These cellular fragments are the components of late-stage dying cells which will be eliminated from the body. The fragments comprise cellular debris and may have occasional nuclear debris that is observed among the cytoplasmic debris. In addition, these cells appear to stain positive for cytokeratin. If the fragments are from prostate cells, then they are PSMA positive as well.

A process leading to the death and destruction of cancer cells can be tentatively formulated through the observation of the terminal cells. In some cases, cancer cells may follow the terminal pathway from FIG. 1A to 1B to 1C to 1D to 1E to 1F. However, the terminal cells depicted by FIGS. 1C to 1D to 1E to 1F comprises one scenario of the terminal pathway. Other variations are possible. For example, other scenarios envisioned include the following terminal paths: 1D to 1F, 1C to 1F, 1E to 1F, 1C to 1D to 1F, 1D to 1E to 1F, and 1C to 1E to 1F. Alternatively, the terminal cell may die or be destroyed at any given cell type, such as at 1C, 1D, 1E, or 1F. In addition, cell types of the proliferative pathway may eventually become terminal cells 1C, 1D, 1E and/or 1F.

The Proliferative Pathway

Proliferative cancer cell types are considered to be positive for cell cycle growth markers, and are viable, growing and/or dividing cancer cells, including dividing cells and cell clusters (microtumors). These subclasses indicate that these cancer cells are living and also dividing in the patient's blood. Proliferative cells are less inhibited, more aggressive, and become self-independent, wherein the cells eventually fail to recognize cellular stimuli such as a hormone, e.g., androgens or estrogens.

Cells that are in the metaphase or M phase comprise one cell type of the proliferative pathway. Metaphase is a stage of cell division in mitosis or meiosis during which the contracted chromosomes (each consisting of two chromatids) are arranged in the equatorial plane of the spindle prior to separation. The existence of these dividing cells may serve as evidence that circulating cancer cells are capable of survival and can undergo mitosis while in the circulation. This subclass comprises two types of cells that are about 25 to 35 micrometers in diameter: 1) an 'early' stage cell is a round cell (FIG. 1B) which may be considered an early dividing cell if it enters the proliferative pathway; and 2) a 'late' stage proliferative cell (FIG. 1G), which may be considered a late dividing cell. FIG. 1G depicts two sister cells, each containing its own nucleus. In addition, both early and late dividing cells exhibit growth potential using cell cycle growth markers such as Ki67 positive cell expression. These cells also show positive cytokeratin expression and depict a typical epithelial network structure.

Another proliferative cell type of is based on the formation of cellular clusters. In general, this cell type is positive for cytokeratin expression, which depicts a typical network structure, and further, the majority of the cells exhibit aneuploidy. If these cells are prostate cells, positive PSMA expression is exhibited. This cell type begins as a cluster of 3 to 4 cells (FIG. 1H) and has the potential, if the environment permits, to grow into a microtumor comprising 5 or more cells (FIG. 1I). A large clump of cells containing over 100 cells is possible. Thus, these microtumors have the ability to develop into large tumor masses. While the significance of the cluster is unknown, the cluster has the ability to circulate, develop into a microtumor, and subsequently arrest in the small veins and/or capillaries. These clusters appear to have a selective growth advantage in a distant site through the recruitment of local nutrients that further promote growth, which leads to invasion of local blood vessels and subsequent vascularization. The cell number and size of each cluster and microtumor vanes. The morphological profile of the cluster is like that of a massive ball with a rough surface. The formation of clusters or microtumors may be the result of clonal growth of circulating cancer cells in the patient's blood. The clusters are an indication that once the circulating cancer cells obtain the ability to survive in the patient's blood, the cells would proliferate through mitotic divisions and clonal growth to form a circulating cancer cell cluster or a circulating microtumor. The microtumor could arrest in the small veins or capillaries and continue to grow when supplied with sufficient nutrients available within the blood vessels. Growth would enable the microtumor to exert pressure on the inside of the vessel. The invasive abilities of and the pressure exerted by these cancer cells could damage the vessel wall. Eventually, the cancer cells would have the opportunity to extravasate and grow around the vessel in a multi-directional manner. As the tumor enlarges, growth factors, such as angiogenic agents, are secreted from the cancer cells which could induce the invaded vessel endothelium to proliferate and form new vessels to vascularize the tumor tissue. The cell types of FIGS. 1H and 1I are established as aggressive cluster of cells. These cell types pose the greatest threat to the patient because of their potential for growth and their association with death.

A process leading to the growth of cancer cells can be tentatively formulated through the observation of the proliferative cells. In some cases, cancer cells may follow the proliferative pathway from FIG. 1A to 1B to 1G to 1H to 1I. However, the proliferative cells depicted by FIGS. 1G to 1H to 1I comprise one scenario of the terminal pathway. Other variations are possible. For example, the cancer cell growth may not progress beyond 1G or 1H. Further, cell types of the proliferative pathway may eventually become terminal cells 1C, 1D, 1E and/or 1F and may die or be destroyed at any given terminal cell type.

The Indeterminate Cell

Another cell type of cancer cells in the Neoplastic Developmental Pathway comprises an indeterminate cell. An indeterminate cell type does not possess definite characteristics which identify the cell as a terminal cell or a proliferating cell. FIG. 1B depicts an intermediate cell that is destined for the terminal pathway or the proliferative pathway. Without wishing to be bound to any particular theory, it appears that the cellular environment and certain stimuli impact the direction of each cell. Thus, these cells are in a "precursor" mode that exists prior to entering the terminal pathway or the proliferative pathway.

The diameter of the indeterminate cells is larger than stem cell-like cells, but smaller than a terminal cell type as shown in FIG. 1C. Indeterminate cells may comprise about 70% of all circulating cancer cells isolated from peripheral blood, including aphereis, since the indeterminate cell type comprises the majority of cancer cells isolated from body fluid samples. These indeterminate cells may develop with more than 1 nucleus, e.g., 2 or more, although 2 is more likely, and fail to undergo cytokinesis. In this case, the indeterminate cell would be targeted for elimination and proceed along the terminal pathway for elimination.

Isolation and Characterization of Circulating Cancer Cells from Body Fluid Samples It is a preferred embodiment of the invention to provide a characterization profile of various biological and molecular markers present within cells isolated from body fluids of animals, preferably, mammals, and more preferably, humans, to help determine the metastatic state of the cancer cells circulating through the body and the nature of the disease/health of the patient.

The methodology disclosed in U.S. Pat. No. 5,962,237 is used to isolate and enumerate cancer cells in a body fluid sample. Examples of body fluids include blood, bone marrow, urine, saliva, lymph fluid, spinal fluid, semen, amniotic fluid, cavity fluids, and tissue extracts. Single, double, or multiple density gradient separation techniques may be used to isolate cancer cells. A double or multiple density gradient separation process is preferred to a single gradient in order to isolate as many cells as possible from the sample, including fragile cancer cells. More preferably, a circulating cancer cell test is used employing double density gradient centrifugation and immunoseparation with or without magnetic cell sorting as an effective and inexpensive method for isolating and enriching white blood cells, which thereby enriches target cancer cells. The enrichment process may include a positive or negative selection process. A "negative selection" process comprises a method of contacting the body fluid with an agent that binds to non-cancer cells and separating the cancer cells from the body fluid, wherein an enriched collection of cancer cells remain. A "positive selection" process comprises a method of contacting the body fluid with an agent that binds to the cancer cells specifically.

The cancer cells may be derived from any different number of cancers, including carcinomas and sarcomas, and in particular, melanoma, glioma, neuroblastoma, fibrosarcoma, rhabdosarcoma, or a hematopoietic tumor of lymphoid or myeloid lineage. The number of circulating cancer cells will vary due to the type of cancer (such as prostate versus breast), the clinical stage of the cancer (such as "early" versus "advanced" disease), variation between patients, and differences in rates of progression or remission in the same patient. For example, a large number of circulating prostate cancer cells, i.e., 50–400 or more cells per 20 ml of blood, have been observed in the blood samples of a few patients diagnosed with prostate cancer. The majority of patients, however, have a small number of circulating cancer cells, i.e., less than 20 cells and many have less than 5 in about 20 ml of blood. Conversely, breast cancer patients appear to have a larger number of cancer cells isolated from body fluid samples than prostate cancer patients, especially "advanced" cases. A characterization profile of a cancer cell population may be used to determine whether the terminal pathway or proliferating pathway is present. Correlation of disease progression in these patients with a dynamic change of the cancer cell types may provide some insight into the relevance of the circulating microtumor hypothesis to the clinical and/or diagnostic settings.

A preferred embodiment of the invention is related to the quantitative measurement and characteristics of the isolated cancer cells in a blood sample, such as peripheral blood or bone marrow. In addition, it is important to monitor any change in the number and to assess descriptive features of these cancer cells. There are several scenarios involving monitoring the number of and assessing characteristics of cancer cells. This process may provide critical information to the physician about the patient's current health status. For example, a prostate cancer patient may have had a prostatectomy and may not have evidence of metastatic cancer for a period of seven or eight years after surgery as determined by current scanning methods. Monitoring the number and characteristics of the patient's cancer cells in body fluid samples over various periods of time, e.g., as best determined by the attending physician may indicate a change in the patient's cancer progression. These assessments of the patient are captured earlier than other methods that are used to obtained information about the metastatic nature of the disease, such as-the use of current scans or before clinical symptoms appear that are indicative of metastatic spread.

Although some blood samples do not have circulating cancer cells, the cells may appear in a blood sample at any time after surgery, radiation, or drug treatment. It is understood that months or years may pass before metastases are measurable. Other blood samples, usually from patients with advanced metastatic disease may have over 350 circulating cancer cells per blood sample, such as in a patient with advanced breast cancer. For example, two breast cancer patients had a large number of cancer cells isolated from blood samples, 350 and 369 or more, respectively. The very appearance of cells that may serve as an indicator that the patient's cancer has escaped beyond an organ and that these "altered" cells are either viable and potentially aggressive killer cancer cells or that the cells have been targeted for elimination from the body. "Altered" means that the cell is no longer a normal cell, which means that the altered cell has developed an aberration wherein the cell has deviated from the usual or normal cell characteristics. More specifically, the altered cell may have developed a mutation(s), e.g, a gene or protein is now altered or a different gene or a different set of genes is now expressed within the cell. Thus, it is important to indicate whether an altered cell can be designated as a terminal cell, including one that is dying, e.g., apoptotic or necrotic, or whether the cell is a proliferative cell. Without being bound to any particular theory, the terminal cell will be eliminated from the body either from the disintegration and/or decomposition of the cell, or alternatively, the cell will be targeted for elimination from the body by scavenger cells, such as macrophages.

About 30 to 50% of breast cancer patients will develop and die from metastatic cancer. Currently, patients diagnosed with breast cancer receive both surgery and drug treatment. A recurrence may take years to develop and currently it is not known which patients will develop metastatic disease. Thus, there is a need to determine whether or not cancer cells exist in a body fluid sample, to take a quantitative measurement of the cells, if any are present, and to assess the cytological descriptive features of these cells. If the patient with cancer is receiving successful drug therapy, decreasing cell numbers and/or dying cells may be found in the blood sample. Early detection of cancer or determining the absence of metastatic activity of circulating cancer cells in body fluid samples may help decide whether lymph node dissection can be eliminated in some patients. In addition, this information may help decide whether the patient's cancer is responding to hormonal therapy, to provide the opportunity to evaluate early indicators for the onset of disease or possible regimens for beginning or terminating therapy, or to determine the patient's response to medical intervention, such as surgery, radiation, and/or drug treatment. The invention presents the opportunity to obtain and characterize cancer cells to provide a characterization profile of the patient in order to assess the status of the cancer for a particular time point to review medical options as a result of this information.

A small number of circulating cancer cells from a body fluid sample, such as about 1 to 5 cells depending upon the cancer type, may be indicative of the need to monitor and assess the patient periodically. For example, a characterization profile may be conducted as an annual test, a biannual test, or testing as recommended by the physician. When no cancer cells are isolated from a body fluid sample, this suggests the absence of metastases. Repeat testing is recommended to confirm this finding. It is important to determine the number and profile of isolated cancer cells, if any exist, after any therapy or surgery, such as a prostatectomy. Again, repeat testing is recommended in order to validate the test results.

Additionally, a cell characterization profile of isolated cancer cells may suggest the appropriate patient population that may benefit from chemotherapy. About 20 to 30% of patients receiving chemotherapy are responders. Monitoring Ithe patients' body fluid samples may help to distinguish responders from non-responders. Preferably, a characterization profile of cancer cells isolated from a body fluid sample(s) for terminal and proliferative features before, during, and after a medical treatment may provide a better indication of the response of the patients. Patients not requiring chemotherapy can be spared severe side effects caused by such treatment through the characterization and assessment of cancer cells. Monitoring cancer patients, patients suspected of having cancer, or patients at risk may assist the physician with an assessment of the patient's health status. The physician can then discuss customized medical care with the patient based upon the compilation of all present test and clinical data. Customized patient care will reduce medical expenses by avoiding unnecessary treatments with the goal of increasing both the quality of life and life expectancy of the patient.

The standard volume collected for screening, monitoring, detecting, isolating, characterizing, and assessing cancer cells is a small volume of a natural body fluid, such as blood, urine, saliva, spinal fluid, semen, vaginal secretions, amniotic fluid, cavity fluids, and tissue extracts or a concentrated body fluid, such as a leukapheresis fraction, a buffy coat sample, and an apheresis sample (U.S. Pat. No. 5,529,903). The volume of the body fluid can vary from 8 to 60 ml, usually about 12 to 25 milliliters (ml). A small volume of blood is advantageous, especially when the cancer becomes more advanced, such as advanced metastatic cancer.

Cancer cell characterization includes elucidating specific cellular activities, such as proliferative ability and invasiveness activity to provide further assessment of the status and nature of the patient's disease state. Long-term monitoring may be valuable to patients that respond initially to treatment and are considered to have recovered (cured), stabilized, or are determined to be in remission. A preferred embodiment of the invention is screening, characterizing, and assessing isolated circulating cancer cells that are difficult to detect by current methodologies. In particular, cancers that fail to be diagnosed in the early stages of disease, such as kidney, pancreas, and ovarian cancers are ideal candidates for screening high risk individuals and especially for individuals after the age of 55. Early detection provides an opportunity for early surgical and/or therapeutic intervention.

Characterization of Circulating Cancer Cells

In a preferred embodiment of the invention, various cell types of cancer cells may be isolated from body fluid samples, e.g., purified or isolated cancer cells from a blood sample, which can then be characterized using a variety of biological, molecular, morphological, and cytological means. Specifically, biological and molecular markers can be used to assess characteristics such as the type of cell origin (such as an epithelial cell), specific type of cell (such as organ type like breast or prostate), cell growth or cell growth potential, cell growth arrest, and hyperploidy status. These cellular markers are selected from, but not limited to, molecular, biochemical, and biological markers and probes that are used alone or in combination Biological and molecular characterization involves measuring and/or analyzing any marker, including, but not limited to, hormones in general, epidermal growth factor, epithelial membrane antigen, estradiol, estrogen, progesterone, androgen, tumor necrosis factor superfamily (such as tumor necrosis factor receptor, FAS, etc.), ferritin, follicle stimulating hormone, actin, gastrin, heat shock proteins, Ki67, lactoferrin, lamin B1, lutenizing hormone, tyrosine kinases, MAP kinase, microtuble associated proteins, c-Myc, myelin basic protein, myoglobulin, pl6, cyclin-dependent kinases, e.g., p21, p53, proliferation-associated nuclear antigen, pancreatic polypeptides, proliferating cell nuclear antigen, prostatic acid phosphastase, prostate specific antigen, pS2, reinoblastoma gene product, S-100 protein, small cell lung cancer antigen, serotonin, somatostatin, oncogene(s), tumor-associated probe(s), alpha fetal protein, β2 microglobulin, CA 19-9 antigen, CA 125 antigen, CA 15-3 antigen, CEA, Cathepsin D, p300 tumor-related antigen, collagen, melanoma, e.g, HMB45, HER-2/neu, e.g, p185, and apoptotic genes and/or proteins, e.g., Bcl-2 subfamily, Bax subfamily, Bh3 subfamily.

Additional markers may include proliferative markers, such as the expression (zero, overexpression or underexpression) or non-expression of p27. Studies to date indicate that the loss of p27 expression by an adenocarcinoma of the prostate correlates with poorer diagnosis and a more aggressive tumor phenotype (Yang, et al., *J. Urology* 159:941–945 (1998); Kallakury, et al., *Cancer* 80:753–763 (1997); Cordon-Cardo, el al., *J. Natl. Cancer Inst.* 90:1284–1291 (1998); Cote, et al., *J. Natl. Cancer Inst.* 90 (12):916–920 (1998)).

The antibodies employed may be labeled with any marker such as a fluorochrome. Such labels are well-known to one of ordinary skill in the art.

Depending upon the type and stage of cancer, some markers may be more relevant than others. For example, CA 125 has been linked to patient survival (Scambia, et al., *Eur. J. Cancer;* 32A(2):259–63 (1996)). CA 15-3 may be more important to the characterization of squamous cell carcinoma antigen (SCC) and implications for chemotherapy in cervical patients (Scambia, supra). Further, the HER-2/neu receptor is elevated or mutated in cancer patients in comparison to cancer-free individuals. Breast cancer patients that overproduce HER-2 protein have poor prognoses. The overexpression of EGF receptor is linked to one-third of all epithelial cancers, such as breast, bladder, kidney, lung, prostate, and head and neck cancers.

In particularly, markers or signals, such as anti-cytokeratin antibodies, may be devoted to characterize the expression of cytokeratin antigen on epithelial cells. Alternatively, specific cell markers are employed. For instance, prostate cell origin in is tested with anti-PSA (Prostate Specific Antigen) and/or anti-PSMA (Prostate Specific Membrane Antigen) antibodies, and/or probes to mRNA for PSMA. The ploidy status (such as polyploidy, hyperploidy, or aneuploidy) may be evaluated using centromeric probes for various chromosomes or the measuring nuclear DNA content in single cells.

Characterization of cancer cells isolated in a body fluid sample may include one or more single cells, a mixture of single cells, and/or microtumors. Different cancer cells may be identified, characterized and counted from each body fluid sample. Different markers may be employed simultaneously. One of ordinary skill in the art would know which markers to employ.

Thymidylate synthetase (TS) expression in the circulating cancer cells may also be assessed. The level of TS enzyme is associated with cellular proliferation and the percentage of cells in S-phase. Maximal cellular TS activity occurs during the S-phase of the cell cycle and is 20-fold higher in rapidly proliferating cells than in nondividing cells. Moreover, the activity of the TS enzyme increases acutely as cell passes from the late $G_1$ to the early S phase of the cycle. However, TS protein is not exclusively associated with the S-phase in asynchronously growing cells. The variation in TS levels between exponentially growing and confluent cell populations appears to be due to differences in TS levels between $G_0$ and $G_1$ cells. The experimental model has been established for semi-quantitative analysis of TS expression in the circulating cancer cells through application of immunocytochemistry staining and fluorescence microscopy (see Example 4).

HER-2/neu expression in circulating cancer cells can also be assessed. The HER2/neu gene (also known as neu and as c-erbB-2) encodes a 185-kDa transmembrane tyrosine/kinase receptor, designated $p185^{HER2}$, that has partial homology with the other members of EGFR (epidermal growth factor receptor) family. Studies of HER-2/neu expression in breast cancer have favored HER-2/neu gene amplification with corresponding overexpression of HER-2/neu protein as predictive of early disease relapse in lymph node-negative and node-positive patients. In prostate cancer, HER-2/neu gene amplification status can determined by FISH on archival prostate cancer specimens, which significantly correlates with high tumor grade and non-diploid DNA content, and is more frequently encountered in tumors with advanced pathological stage. FISH is more sensitive than immunocytochemical staining for detection of abnormalities in the HER-2/neu gene. A set of techniques has been completed for analysis of HER-2/neu gene copy number by FISH and semi-quantitative analysis of HER-2/neu protein expression by immunocytochemical stain in circulating cancer cells (see Example 5, FIGS. 5A and 5B).

p27 and Ki67 expression of cancer cells are additional markers for characterizing and assessing terminal and proliferative cells. Analysis of tumor growth fraction has become essential for the treatment of malignancies. The recent development of monoclonal antibodies to proliferation-related nuclear antigens has made the assessment of tumor proliferative activity by immunocytochemical techniques quite feasible p27/kip1 (p27) is a member of the universal cyclin-dependent kinase inhibitor (CDKI) family. p27 expression is regulated by cell contact inhibition and by specific growth factors, such as transforming growth factor (TGF)-beta. Since the cloning of the p27 gene in 1994, a host of other functions have been associated with this cell cycle protein. In addition to its role as a CDKI, p27 is a putative tumor suppresser gene, a regulator of drug resistance in solid tumors, and promoter of apoptosis. p27 also acts as a safeguard against inflammatory injury and has a role in cell differentiation. The level of p27 protein expression decreases during tumor development and progression in some epithelial, lymphoid, and endocrine tissues. This decrease occurs mainly at the post-translational level with protein degradation by the ubiquitin-proteasome pathway. A large number of studies have characterized p27 as an independent prognostic factor in various human cancers, including breast, colon, and prostate adenocarcinomas. The role of p27 in the regulation of the cell cycle and other cell functions as well as a diagnostic and a prognostic marker in human neoplasms aids in the characterization of cancer cells of the present invention.

Ki67 monoclonal antibody detects a human nuclear antigen present in proliferating, but not quiescent cells. In fact, Ki67 antigen is present in S-, G1-, G2-, and M-phases of the cell cycle, and thus Ki67 labeling marks the whole population of proliferating cells. The Ki67 immunocytochemical staining has diagnostic and prognostic value that as evident in many studies showing significant correlation between the mean values of the growth fraction determined by Ki67 immunocytochemical staining and the S-phase fraction as measured by flow cytometry as well as histopathological parameters of various human malignancies (see FIGS. 11A and 11B).

p53 expression in circulating cancer cells may also be assessed. More than 100 single gene disorders have been associated with high-risk tumor development. Great focus has been placed on the research of the tumor suppressor gene, p53, in particular. Alterations of the p53 tumor suppressor gene are associated with advanced stage prostate carcinoma. Mutated p53 arise at certain times during the progression of tumors, for example, in the emergence of a carcinoma in situ from benign lesions of the colon, testis, and prostate. Mutations of p53 sometimes coincide with more aggressive neoplasms, which have been described to be resistant to chemotherapy, radiotherapy, and hormonal therapy. Thus, expression of the mutant p53 protein may be prognostic in, inter alia, prostate cancer (see FIGS. 7A and 7B).

Two distinct modes of cell death, apoptosis and necrosis, can be distinguished based on differences in morphological, biochemical and molecular changes of dying cells. Apoptosis (programmed cell death) is the most common form of eukaryotic cell death. It is a physiological suicide mechanism that preserves homeostasis in which cell death naturally occurs during normal tissue turnover. Thus, apoptosis may be defined as a method of programmed cell death that is useful to eliminate designated cells from the body.

The nuclear collapse in apoptosis is associated with extensive damage to chromatin and DNA-cleavage into oligonucleosomal length DNA fragments after activation of a calcium-dependent endogenous endonuclease. However, very rare exceptions have been described where morphological features of apoptosis are not accompanied with oligonucleosomal DNA cleavage.

Apoptosis is essential in many physiological processes. In oncology, extensive interest in apoptosis comes from the observation that this mode of cell death is triggered by a variety of antitumor drugs, radiation and hyperthermia, and that the intrinsic propensity of tumor cells to respond by apoptosis is modulated by expression of several oncogenes and may be a prognostic marker for cancer treatment. Apoptotic detection of circulating cancer cells serves as an important method to further characterize cancer cells, especially metastatic cancer cells.

Several methods have been described to identify apoptotic cells. Bcl-2 expression is a useful marker for apoptotic activity in further evaluating circulating cancer cells. Bcl-2 is involved in the control of apoptosis in a range of different cell types. The gene Bcl-2 was originally isolated and mapped to the t(14;18) translocation breakpoint common in non-Hodgkin's lymphomas. Two genotypes, which are not identical, Bcl-2 and Bcl-XL may play qualitatively different roles during development. Bcl-2 and Bcl-XL can determine the fate of a cell under conditions in which they are expressed aberrantly, but do not necessarily help us to interpret their role in the regulation of apoptosis in normal cells. Recently, the clinical research data showed that overexpression of Bcl-2 occurs frequently in prostate cancer and is associated with both hormonal therapy and chemotherapy resistance. In experimental systems, Bcl-2 overexpression occurs after androgen deprivation and transfection of Bcl-2 into sensitive cell lines makes them resistant to chemotherapy and hormonal therapies. Bcl-2 can be inactivated by phosphorylation as occurs with taxanes. The retinoids, as a class, can inhibit the growth of resistant cell lines that overexpress Bcl-2, and the combination of interferon (IFN) and cis-retinoic acid (CRA) has been demonstrated to increase antitumor activity. FIG. 6 depicts LnCap cells which were immunocytochemically stained with an anti-cytokeratin antibody and a Bcl-2 antibody.

Another method that is useful to identify apoptotic activity is to measure nucleotide incorporation, which may be used to discriminate apoptosis from necrosis. One specific test is TUNEL staining for the detection of circulating cancer cell death (see FIGS. 9A, 9B, and 10).

In addition, after staining, several signals are detected in the cancer cell cytoplasm. The cytokeratin staining produces a network that covers areas of cytoplasm and nucleus comprising thick, intensely fluorescent filaments. The anti-PSMA antibody staining results in homogenous signal intensity in the central cytoplasm, with more intense staining at the edge of the cytoplasm. This forms a fluorescent rim at the outermost edges of the cancer cell. The cancer cell nucleus also varies in shape with DAPI (4',6-diamidino-2-phenylindole) staining. Nuclear morphology can be irregular, elliptical, or round.

Figure 3:
FIG. 3 is a monochromatic image depicting cancer cells and white blood cells for quantitative DNA content analysis.

Nuclear DNA quantitative analysis shows binding of DAPI to DNA in the cell nucleus with high binding specificity to exhibit intense fluorescence of the complex. The DNA quantitative analysis is based on a comparison of the DNA content of a reference cell, white blood cells (WBCs) with the circulating epithelial cancer cells in question. Circulating WBCs, in the $G_0$ phase of the cell cycle, have 2 copies (2c) of DNA content, which equals 2N. Normal epithelial cells in $G_0$ to $G_1$ phase (not dividing) also have 2c DNA and at $G_2$ to M phase have 4c DNA (dividing). Therefore, a ratio of the reference WBC DNA content to cancer cell DNA content greater than two if dividing and one if not dividing is a specific measure of aneuploidy (see Example 3, FIG. 3, Table 2).

Characterizing prostate cancer cells and learning about their mutations in the region of the androgen receptor gene has always been of keen interest to the attending physician. One of the molecular descriptions for prostate cancer cells is a mutation of the gene for the androgen receptor, which is related to the treatment of prostate cancer by an androgen antagonist. If the mutation is such that the receptor will no longer bind to the antagonist, then drug treatment will no longer be effective. Furthermore, if the androgen receptor mutates to the extent that it will bind the antagonist and trigger a natural androgen response, then the antagonist becomes an agonist that will encourage the growth of prostate cancer cells containing the mutated androgen receptor. Thus, androgen receptor (AR) expression of cancer cells is another measurement that may be added to the characterization profile of the patient. Androgen receptor concentration has also been demonstrated to be prognostic in a subgroup of patients with high Gleason scores. The studies indicated that tumor specimens that lacked AR receptor in the Gleason score range between 7 and 9 had a significantly poorer prognosis. More aggressive tumors are associated with a lack of AR which suggests that these tumors may be less sensitive to hormonal manipulation.

Chromosome examination of cancer cells is yet another method of characterization. Chromosomal centromere probes could be designed, and synthesized for the cytogenetic analysis of circulating cancer cells. Characterizing circulating cancer cells, which are continuously evolving in their neoplastic progression at the molecular level, i.e., genetic variations/mutations, and at the gene expression level, i.e., mRNA or protein, is a common goal of cancer researchers.

FISH can be used, not only to determine overall ploidy, but also to assess the over-representation or under-representation of specific chromosomes in interphase cells. For example, FISH can be performed using CY3 labeled chromosome 18 on LnCap prostate cancer cell lines. Aneuploidy of chromosome 18 is routinely evident in prostate cancer. As mentioned previously, measuring the DNA content of the cell in question is also a way to determine whether the cell is aneuploid.

Patients who undergo surgery for early cancer may also benefit from more accurate staging derived from pathological examination of the surgical specimen. Recent results from 200 surgical prostate patients at the Johns Hopkins University Hospital indicate that 68.5% of patients had organ-confined disease, 28% had extra-prostatic extension, 3.5% had seminal vesicle involvement, and 3% had lymph node metastases (unpublished data). The correlation of pathological results and the future course of disease progression has been quite well established. However, it has been reported that about 20 to 30% of the 68.5% of patients determined to have organ-defined disease will develop a recurrence which may result in death. Furthermore, it is important to note that this information is only available to the patients and their attending physicians after the surgery, not before the decision is made for surgery. Furthermore, this critical pathological information would not be available to patients who elect not to have surgery. Prostate cancer patients who opt for "watchful waiting" would have access to continuous monitoring of circulating cancer cells that may assess the progressive nature of the disease, especially the metastatic nature. Additionally, information is important for patients receiving radiation therapy as to which patient will most likely have a recurrence. It is possible to correlate the initial remission, cure, or subsequent recurrence with both pre- and post-radiation, PSA levels, and the characterization profile of cancer cells within the scope of the invention. More specifically, this information will be predicted by the presence or absence of circulating cancer cells before irradiation and after certain intervals following irradiation.

Isolation of Circulating Cancer Cells—Density Gradient Separation

Although various methods may be used to isolate cancer cells from body fluid samples, density gradient centrifugation separation is a preferred method of the present invention. Generally, density gradient separation processes involve preparing one or more layers of gradient media, wherein the density or densities of the gradient media should be higher than the density of the cancer cells to be separated. The fluid to be processed is placed onto the upper layer of the gradient medium (or uppermost layer of the gradient medium) and the media and the fluid are centrifuged until the components of the fluid separate form one another according to their individual component densities.

A variety of density gradient media and protocols for carrying out density gradient separation are suitable for carrying out this invention. Thus, single and/or multiple density columns can be used, and any suitable combination of media densities can be employed. Of course, density gradient separation according to this invention can also be carried out using continuous and/or discontinuous gradients. Different media and protocols can be utilized depending on the fluid to Mbe processed and the cells of interest. Density gradient separation can be carried out any number of times to provide one or more fluids having an increased concentration of cancer cells. The gradient medium or media can also include one or more additives, for example, to provide a desired density or viscosity. See U.S. Pat. No. 5,962,237.

Preferably, methods of isolation allow different densities of cancer cells, e.g., "light" and "heavy" cancer cells to be processed differently, yet captured from the same sample using a double density gradient. Although those skilled in the art will be able to determine the appropriate densities, in the specific case of enriching circulating cancer cells in natural and unconcentrated body fluids containing WBC and cancer cells, the gradient medium (gel) should have a density ranging from about 1.06 g/ml to about 1.10 g/ml, with about 1.068 g/ml to about 1.083 g/ml being preferred.

Those skilled in the art will be able to determine the appropriate densities for enriching circulating cancer cells in concentrated body fluids, such as a buffy coat or a leukapheresis sample, which contains WBC and may contain cancer cells. The gradient medium (gel) should have a density between about 1.06 g/ml and about 1.083 g/ml, wherein specifically, the density is no less than 1.06 g/ml, more preferably no less than about 1.068 g/ml, and most preferably a density of about 1.070 g/ml. Generally, the volume of a concentrated body fluid from one patient for isolating circulating cancer cells is between 10 to 500 ml, preferably between 50 to 180 ml (higher volumes are indicative of an apheresis separation procedure).

A multiple density gradient is preferred in order to isolate as many cancers cells as possible, including the fragile, lighter cancer cells that are difficult to retrieve intact with a single density gradient. Thus, a double density gradient protocol is preferred to isolate circulating cancer cells in natural body fluids, wherein a first density gradient medium is about 1.068 g/ml to about 1.077 g/ml, preferably about 1.068 g/ml, and a second density gradient medium is about 1.077 g/ml to about 1.083 g/ml, preferably about 1.077 g/ml. Six regions are formed after centrifugation. The six regions formed after centrifugation are Plasma, Interface I, Interface II, Gradient I, Gradient II, and a Pellet (WO 97/38313; U.S. Pat. No. 5,962,237). A first fluid suspension is formed comprising the combination of the Interface I and Gradient I fractions, which contains an increased concentration of the "lighter" cancer cells. Generally, these lighter A cancer cells are fragile, large, and/or sticky. A second fluid suspension is formed comprising the combination of the Interface II and Gradient II fractions, which contains an increased concentration of the "heavier" cancer cells. Generally, these heavier cells are smaller than the lighter cells captured in the first fluid suspension. A binding agent can be added to the second fluid suspension that binds non-cancer cells which may then be removed from the second fluid suspension to provide a second fluid enriched with a greater concentration of cancer cells. The first fluid suspension may be combined with the second fluid suspension before or after the step involving the removal of non-cancer cells.

Cancer cells may be enriched further by a "negative selection" process. Negative selection involves the use of a binding agent that binds the non-cancer cells, e.g., white blood cells in some body fluids and/or red blood cells in others, for removal from the cell fraction harvested from the gradient. Preferably, the second fluid suspension is treated with the binding agent and not the first fluid suspension.

Leukapheresis, apheresis, or buffy coat concentrate samples are obtained using standard protocols known in the literature. Gradient centrifugation is conducted by diluting the sample with 1×PBS up to about 30 ml and loading the diluted sample on an about 1.077 g/ml histopaque gradient. Forty microliters of the diluted sample are loaded carefully on 10 ml of gradient (per tube). Next, the tubes are centrifuged at about 600×g for about 30 minutes at about 20° C. After centrifugation, the interface is collected from each tube and is washed with 1×PBS. Next, the cells are pelleted by about 200×g centrifugation. Then, either magnetic cell sorting or biotin-avidin positive isolation is conducted to collect fluid enriched with cancer cells, if any are present.

Magnetic Cell Soring System (a) The cells in 0.1% BSA are incubated with 1:10 KS antibody (mouse IgG1: epithelial surface antibody which can be obtained commercially) on ice for 30 minutes and then washed with PBS and pelleted by centrifugation at 60×g for 10 minutes.

(b) The cells in 0.1% BSA are incubated with 1:4 goat anti-mouse IgG microbeads (Miltenyi Biotec; Order-No. 48401) on ice for 30 minutes. After incubation with the microbeads, the cells are washed with PBS and pelleted by centrifugation at 60×g for 10 minutes. The cells are resuspended in 1.0 ml of 0.1% BSA.

(b1) MidiMacs separation system: MidiMacs separation column is placed on a magnetic field. The column is rinsed with 2.0 ml of 0.1% BSA. The cell suspension is then loaded onto the column and allowed to pass through the column. The cell suspension is then collected from the column, reloaded onto the column and passed through the column once again. The cell suspension is subsequently collected from the column as a negative collection of unwanted WBC.

(b2) The column is removed from the magnetic field and eluted with 1.0 ml of 0.1% BSA. The same elution of the column with 1.0 ml 0.1% BSA is repeated four times with the last two elutions under pressure. The eluted cell suspension is collected as a positive collection of cancer cells.

(c) Slide preparation using 2.0 ml of 4.0 ml positive collection from the magnetic separation column for each slide preparation: the 2.0 ml cell suspension is loaded into a Megafunnel with a charged slide and cytospun at 1000 rpm for 10 minutes at RT. The slide is then air-dried at RT for at least two hours.

Biotin-Avidin Positive Isolation System:

(a) Materials: Epithelial surface antibodies (mouse IgG1 which can be obtained commercially), anti-mouse IgG antibody-Biotin (KPL, Inc.; Cat. No. 176–1806), Sepharose 6 MB (Pharmacia Biotech; Code No. 17-0820-01), Avidin (Sigma; Lot. 46H9540), and Avidin-Sepharose 6 MB beads for column preparation.

(b) The cells in 0.1% BSA are incubated with 1:10 KS antibody (mouse IgG1: epithelial surface antibody) on ice for 30 minutes, washed with PBS and pelleted by centrifugation at 60×g for 10 minutes. The cells in 0.1% BSA are then incubated with 1:20 goat anti-mouse IgG-Biotin on ice for 30 minutes. After immunocytochemistry incubation, the cells are washed in PBS and pelleted by centrifugation at 60×g for 10 minutes. The cells are then resuspended in 2.0 ml of 1.0% BSA.

(c) Cell Separation: the cell suspension is loaded onto the Avidin bead column and incubated at RT for 15 minutes. The column is then eluted with 10 ml of 1.0% BSA, followed by an elution with 5.0 ml of PBS to remove the unwanted WBC. Cancer cells are detached from the avidin beads using mechanical force. The cancer cells are then eluted from the column using 5.0 ml of 0.1% BSA. The eluted cell suspension is collected as a positive collection of cancer cells.

(d) Slide preparation using 2.5 ml of 4.0 ml positive collection from the avidin separation column for each slide preparation: the 2.5-ml cell suspension is loaded into a Megafunnel with a charged slide and cytospun at 1000 rpm for 10 minutes at RT. The slide is then air-dried at RT for at least two hours.

The following examples are illustrative, but not limiting, of the methods of the present invention. Other suitable modifications and adaptations of the variety of conditions normally encountered which are obvious to those skilled in the art are within the spirit and scope of the present invention.

EXAMPLE 1

Cancer Cell Isolation Methodology and Idendfication

This example illustrates the cancer cell isolation methodology and identification of micrometastasis and other circulating cancer cell populations in prostate blood samples of patients diagnosed with prostate cancer.

Blood Collection

With informed consent, 10–20 ml of blood was drawn from the antecubital veins of control subjects and patients with prostate and breast cancer into Vacutainer tubes (Becton Dickinson; Franklin Lakes, N.J.) containing acid citrate dextrose (ACD) solution A as an anticoagulant. The samples were processed at room temperature via the isolation procedure described below within 24-hour hours, including the transport time. All protocols and consent forms were IRB (Institutional Review Board) by collaborating institutions.

Double Density Gradient Centrifugation (Prostate)

About 10 to 20 ml of blood were diluted to 30 ml with PBS at room temperature in a 50 ml polypropylene tube. Tubes were capped and mixed gently by inversion three to six times. With a 20 ml syringe and pipetting standard blunt end stainless steel needle (Popper & Sons, Inc.; New Hyde Park, N.J.), 10 ml of each gradient (density of 1.068 g/ml and 1.077 g/ml, respectively) was aspirated and loaded into the bottom of the tube. The tube was centrifuged at 400×g for 30 minutes at 20° C. with no brake. The first and second interfaces were collected along with gradient (about 10 ml) using a disposable transfer pipette into two new 50 ml polypropylene tubes. The $1^{st}$ Interface collection was diluted to 40 ml with Hank's Balanced Salt Solution. The $2^{nd}$ Interface collection was diluted to 40 ml with PBS. Both tubes were mixed gently by inversion. Tubes were centrifuged at 160×g for 10 minutes at 20° C. with low brake. The supernatant was gently aspirated using a 25 ml pipette or vacuum pump and the cell pellet was kept at the bottom of each tube. Next, the first interface cell pellet was resuspended with PBS (QS'd to 45 ml). The second interface cell pellet was resuspended with approximately 5–10 ml of Lysing Buffer and allowed to stand for approximately 3–5 minutes at RT. After standing at RT, the second interface suspension was diluted with PBS (QS'd to the 45 ml). Both interface solutions were centrifuged at 300×g for 10 minutes at 20° C. with low brake. The supernatants from the two interface solution cell pellets from each tube were gently aspirated using a 25 ml pipette or vacuum pump and the cell pellet was kept at the bottom of each tube. The first interface pellet from 1.068 g/ml gradient isolation was resuspended with 2.0 ml of 0.1% BSA and refrigerated at 2–8° C. for cytospin preparation.

Double Density Gradient Centifugation (Breast)

About 10 to 20 ml of blood were diluted to 30 ml with PBS at room temperature in a 50 ml polypropylene tube. Tubes were capped and mixed gently by inversion three to six times. With a 20 ml syringe and pipetting standard blunt end stainless steel needle (Popper & Sons, Inc.; New Hyde Park, N.J.), 10 ml of each gradient (density of 1.068 g/ml and 1.083 g/ml, respectively) was aspirated and loaded into the bottom of the tube. The tube was centrifuged at 40.0×g for 30 minutes at 20° C. with no brake. The first and second interfaces were collected along with gradient (about 10 ml) using a disposable transfer pipette into two new 50 ml polypropylene tubes. PBS was added to these new tubes containing the interfaces up to 40 ml and mixed gently, but thoroughly by inversion. Tubes were centrifuged at 258×g for 10 minutes at 20° C. with low brake. The supernatant was gently aspirated using a 25 ml pipette or vacuum pump and the cell pellet was kept at the bottom of each tube. The first interface cell pellet was resuspended with Hanks Balanced Salt Solution 1×(without Ca or Mg) up to 20 ml. The second interface cell pellet was resuspended with Lysing Buffer up to 20 ml. While mixing on the Orbitron Rotator II (Boekel Scientific, Model 260250), the second interface cell suspension was incubated for 5–10 minutes at RT. After incubation, both interface cell suspension tubes were centrifuged at 160×g for 10 minutes at 20° C. with no brake. The supernatants from the two interface cell suspension tubes were gently aspirated using a 25 ml pipette or vacuum pump and the cell pellet was kept at the bottom of each tube. The first interface pellet from the 1.068 g/ml gradient isolation was resuspended with 1.0 ml of 0.1% BSA and refrigerated at 2–8° C. for Cytospin preparation.

Magnetic Cell Sorting

The second interface pellet from the 1.077 or 1.083 g/ml gradient isolations was then resuspended with 1.0 ml of 0.1% BSA and kept at 2–8° C. for magnetic ceillsorting. Magneticbeads CD45-mouse-anti-humanIgG(Dynal beads M450, Dynal; Oslo, Norway) were suspended thoroughly by inversion before use. Three hundred microliters of beads were pipetted and added to a 5 ml polypropylene tube. The beads were washed by pipetting 3.0 ml of 0.1% BSA into the 5 ml tube. This tube was placed on the Magnetic Particle Concentrator (Dynal; Oslo, Norway) to for one minute at RT. The supernatant was then aspirated and discarded to remove sodium azide and free antibody. The cell suspension from the 1.077 or 1.083 g/ml gradient (about 1.0 ml) was then transferred to the tube containing the washed CD45 beads. Remaining cells were washed from the wall of the tube with 1.0 ml of 0.1% BSA and transferred to the tube containing the magnetic beads for a total volume of approximately 2.0 ml. The cells were incubated with the beads at 2–8° C. for 30 minutes at 10 rpm on an Orbital Sample Mixer (Dynal; Oslo, Norway). The tube was then placed on the Magnetic Particle Concentrator for two minutes at RT. Next, the supernatant from the CD45 negative collection was transferred to the back to the 50 ml tube containing the 1.068 g/ml interface suspension. After mixing the two interface suspensions, the cell suspension (total of approximately 4 ml) mixture was cytospun in a Megafunnel™ Disposable Sample Chamber (Shandon, Inc.; Pittsburgh, Pa.) at 1,000 rpm for 10 minutes at room temperature, and slides were air-dried for at least two hours before staining.

Immunocytochemistry Staining

Slides were fixed in 2% paraformaldehyde for 15 minutes, then rinsed two times with 1×PBS after fixation. Slides were then incubated in PBS for 10 minutes at room temperature. The volume of the incubation mixture for immunostaining was 30 ml. The basic mixture contains a permeability buffer and anti-cytokeratin antibody diluted 1:3 FITC (CAM5.2, Becton-Dickinson, San Jose, Calif.). For prostate cancer cells, an antibody against PSA (Dako; Carpinteria, CA or an antibody against PSMA (Horoszewicz, et al., *Anticancer Res.* 7:927–36 (1987)) is added. Antibodies against PSMA from hybridoma cultures 7E11-C5 and 9H10-A4 (ATCC Nos. HB-11430 and HB-10494) and J591 (Liu, et al., *Cancer Res.* 57:3629–34 (1997)) (generously donated by Dr. Neil Bander at New York Hospital-Connell Medical Center) have been produced.

To further characterize the cancer cells the following antibodies may also be added to the incubation mixture: anti-P27-cy5, anti-Ki67-cy3 (both from Transduction Laboratory, used at 5 ng/$\mu$l); Her-2/Neu (Dako, Rabbit anti-human antibody—use 1:20 dilution for 2 hours at 4° C./$2^{nd}$ antibody: Goat anti-rabbit IgG FITC conjugate, use 1:50 dilution in 0.1% BSA for 1 hour at RT); BCL-2 (Dako, Mouse anti-human antibody—use 1:20 dilution in 0.1% BSA for 2 hours at 4° C./$2^{nd}$ antibody: Goat anti-mouse IgG (H+L) Texas Red conjugate, use 1:50 dilution in 0.1% BSA for 1 hour at RT); p53 (Dako, 1:20 dilution with 0.1% BSA for 2 hours at 4° C./$2^{nd}$ antibody: Goat anti-mouse IgG (H+L) Texas Red conjugate, use 1:50 dilution in 0.1% BSA for 1 hour at RT); anti-androgen receptor (detected with secondary antibody); and anti-thymidylate synthetase (TS, detected with secondary antibody). Primary antibodies that are detected with fluorescent secondary antibodies must be incubated with the cells, washed and incubated with the second antibody prior to incubation with the basic anti-cytokeratin antibody mixture. A coverslip is placed on the sample area, and, in most cases, incubated at room temperature for 60 minutes in a moisture box. Coverslips were then removed from the slides, and slides were washed in a Coplin Jar containing 1×PBS at room temperature for 10 minutes. Finally, slides were air-dried for 10 minutes at room temperature. The dilutions various above follow a universal dilution of 100–200 nanograms antibody per 50 microliters buffer.

Fluorescent In Situ Hybridization (FISH)

The slides were dehydrated using 75%, 85% and 95% alcohol in a Coplin Jar for one minute at each concentration. Next, slides were dried for 10 minutes at room temperature. FISH Cocktail (vol./slide) was prepared using either 19 ml of FISH buffer with 1.0 ml of chromosomal centromere probes, PSMA mRNA probes, or an androgen receptor gene probe (Vysis; Downers Grove, Ill.). FISH cocktail was added to the sample area on the slide, covered with a coverslip, and sealed with rubber cement. Samples were denatured at 85° C. for 5 minutes on a hot plate. Samples were then placed in a moisture box and hybridized in a 42° C. oven for 4 hours. After hybridization, rubber cement and coverslips were carefully removed from the slide. Slides were washed in a Coplin Jar containing 2×SSC/0.1% NP-40 (ISB, Cleveland, Ohio) at 42° C. (preheated) for 2 minutes, then air-dried at room temperature. Samples were counterstained with DAPI in mounting medium (1.0 g/ml) (Vector Lab; Burlingame, Calif.), covered with a coverslip, and sealed with FLO-TEXX mounting medium (Lemer Lab; New Haven, Conn.). The slides were placed in a dark area at room temperature for at least 10 minutes. Analysis of stained slides was conducted using computerized fluorescence microscopy. Positive cancer cells were imaged and stored in a computer.

TUNEL (TdT-Mediated dUTP Nick End Labeling) Staining

After fixation of 2% paraformaldehyde, the slide was washed in PBS for ten minutes, then, passed through 0.1%

Triton X-100 buffer. TUNEL reaction mixture (Boehringer Mannheim) (see below) and cytokeratin antibody were added on the sample area on the slide, and the slide was incubated at 37° C. for 60 minutes.

Preparation of the TUNEL Reaction Mixture

One hundred μl of Label Solution from bottle 2 (Boehringer Mannheim) was removed for two negative controls. The total volume of bottle 1 (50 μl) (Boehringer Mannheim) was added to the remaining 450 μl Label Solution in bottle 2 (Boehringer Mannheim) to obtain 500 μl TUNEL reaction mixture. The combination was mixed well to equilibrate the components and 50 μl was added to each sample and control. Slides were washed with PBS in a Coplin Jar containing 1×PBS at room temperature for 10 minutes. Finally, slides were air-dried for 1 minutes at room temperature. Samples were counterstained with DAPI in mounting medium (1.0 g/ml) (Vector Lab; Burlingame, Calif.), covered with a coverslip, and sealed with FLO-TEXX mounting medium (Lerner Lab; New Haven, Conn.). The slides were placed in a dark area at room temperature for at least 10 minutes. Analysis of stained slides was conducted using computerized fluorescence microscopy. Positive cancer cells were imaged and stored electronically. The slides were designed for positive and negative control.

Positive Control

Prostate cancer cells, such as LnCap, DU145, TSU-PR1 (gift from Alan Partin, Johns Hopkins University), and PC-3, and breast cancer cells MCF-7 and T47D (ATCC Nos. CRL-1740 (LnCap), HTB-81 (DU145), CRL-1439 (PC-3), HTB-22 (MCF-7), and HTB-133 (T47D)) were cultured with RPMI 1640 media (Sigma; St. Louis, Mo.) with 10% fetal bovine serum (Gemini Bio-products Inc.; Calabasas, Calif.). Cultured cancer cells were detached from the culture flask using a trypsin wash. The density of the LnCap cells was determined by counting cells in a spot smear on a slide. In general, a small volume of blood, e.g. 10 to 20 ml, is taken from controls without cancer. LnCap cells were spiked into the control sample and the spiked blood was subjected to the complete isolation protocol and staining procedure. Percent recovery was calculated and staining quality was checked by microscopy.

Negative Control

With informed consent, 10 to 20 ml of blood from 20 females and 43 males without cancer were collected as a negative control sample. The blood samples were subjected to the complete isolation protocol and staining procedure discussed in this example. Stained slides were examined by microscopy. In the female control samples, no circulating epithelial cells were found. Three (7%) of the 43 male controls had circulating epithelial cells, but these cells lacked prostate specific signals and chromosome aneuploidy. Average prostatic circulating cell numbers from the positive detection patients were 17.28±37.45 (mean±SD, N=106) and the median number was 5 (1–259 cells) in 10 to 20 ml of blood.

Recovery Study

A recovery study was designed to test assay sensitivity. Blood from cancer-free adult females was spiked with LnCap cultured cells. In the first group, 10 ml of blood with $6.64 \times 10^7$ to $2.32 \times 10^8$ leukocytes were spiked with 100 LnCap cells. Average recovery was 88.4% (N=10). In the second group, 20 ml of blood with $2.20 \times 10^8$ leukocytes were spiked with 12 LnCap cells (N=4), and 35 LnCap (N=6) cells, respectively. Recovery was 80% (58–97%; N=10).

EXAMPLE 2

Morphological Analyses of Circulating Cancer Cells

This example shows the data for the neoplastic developmental pathway. The identification of cell types of circulating cancer cells for characterization is based upon cytological analysis to assess whether the cells are terminal or proliferative. The role of these isolated cells in the formation of circulating microtumors and resultant metastases is also of interest.

Cancer cells from 18 breast cancer patients were isolated according to the methodology set forth in Example 1. Based on the dynamic neoplastic developmental pathway, the cells were imaged and viewed using a computerized fluorescent microscope to determine the cell types are set forth in FIGS. 1A–1I FIGS. 2A–2S are monochrome images of the cell types depicted in FIGS. 1A–1I. FIGS. 2 through 1I depict monochrome images of cellular cytokeratin staining ("CK") (CAM 5.2 labeled with FITC), thymnidylate synthetase staining (TS monoclonal antibody conjugated to FITC), dUTP labeled with FITC staining, and Her-2/neu monoclonal antibody (Her-2/neu conjugated to FITC) staining of a cell type using a filter cube with a 470/40 nm exciter, a 497 nm dichroic and a 522/40 emitter. A cell nucleus (nuclei) ("Nucleus") stained with DAPI was obtained using a filter cube with a 360/40 nm exciter, a 400 nm dichroic, and a 470/40 nm emitter. PSMA, cytokeratin, Bcl-2, p53, KS monoclonal antibody staining and androgen receptor (ADR) monoclonal antibody conjugated to Texas Red staining were obtained using a filter with a 581/10 nm exciter, a 593 nm dichroic and a 617/40 nm emitter. p27 nuclear antigen staining (p27 monoclonal antibody conjugated with CY5) was obtained using a filter cube with a 630/20 nm exciter, a 649 nm dichroic and a 667/30 nm emitter. Ki67 nuclear antigen staining (Ki67 monoclonal antibody conjugated to a CY3 fluorescent marker) was obtained using a filter cube with a 546/11 nm exciter, a 557 dichroic and a 567/15 nm emitter.

Figure 2A:
FIGS. 2A–2S are monochromatic images of the cell types depicted in FIGS. 1A–1I.
Figure 2B:
Figure 2C:
Figure 2D:
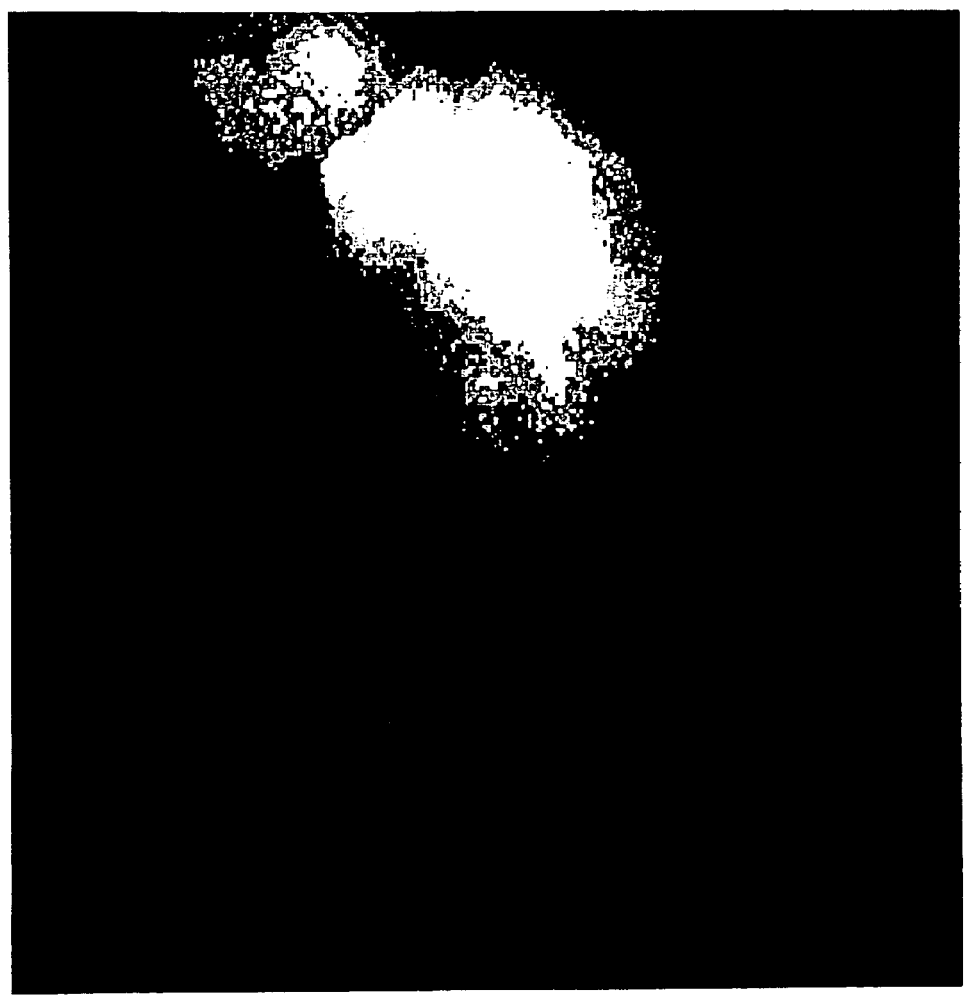
Figure 2E:
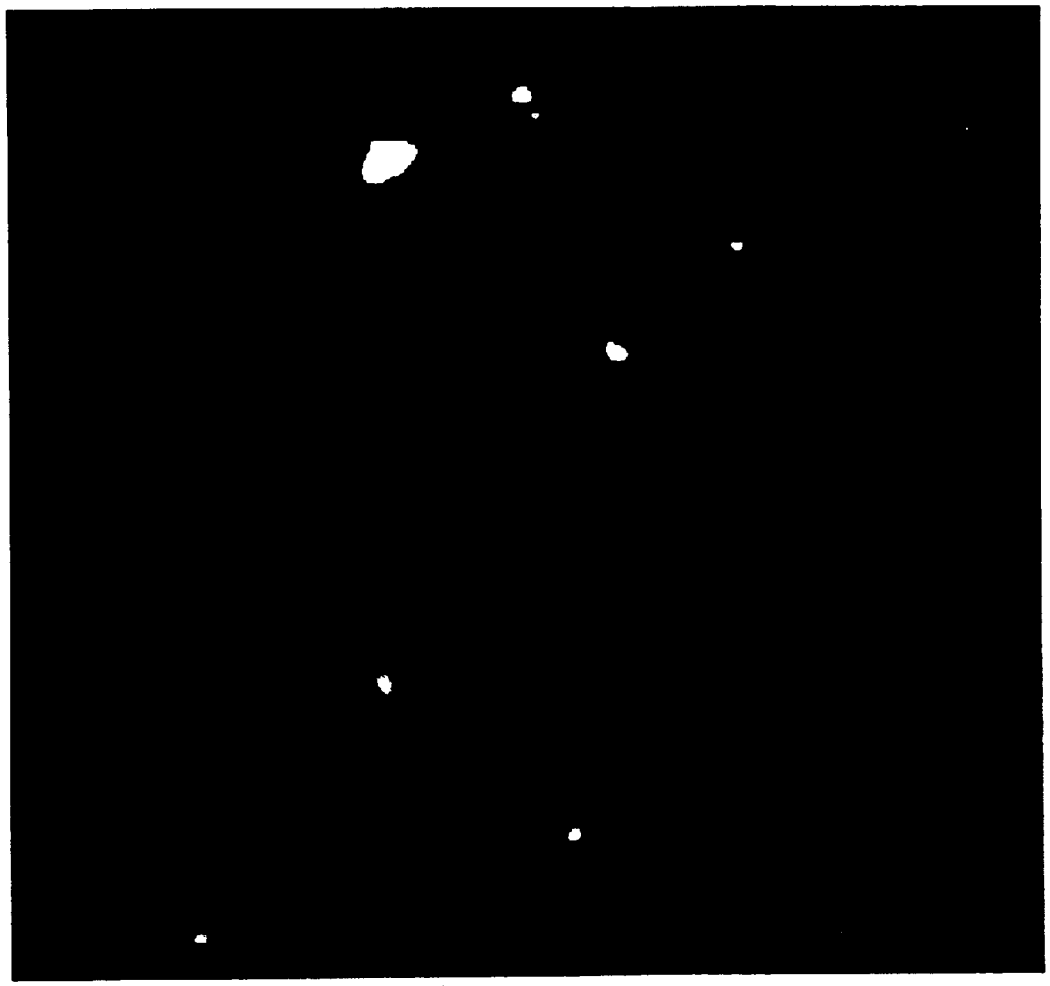
Figure 2F:
Figure 2G:
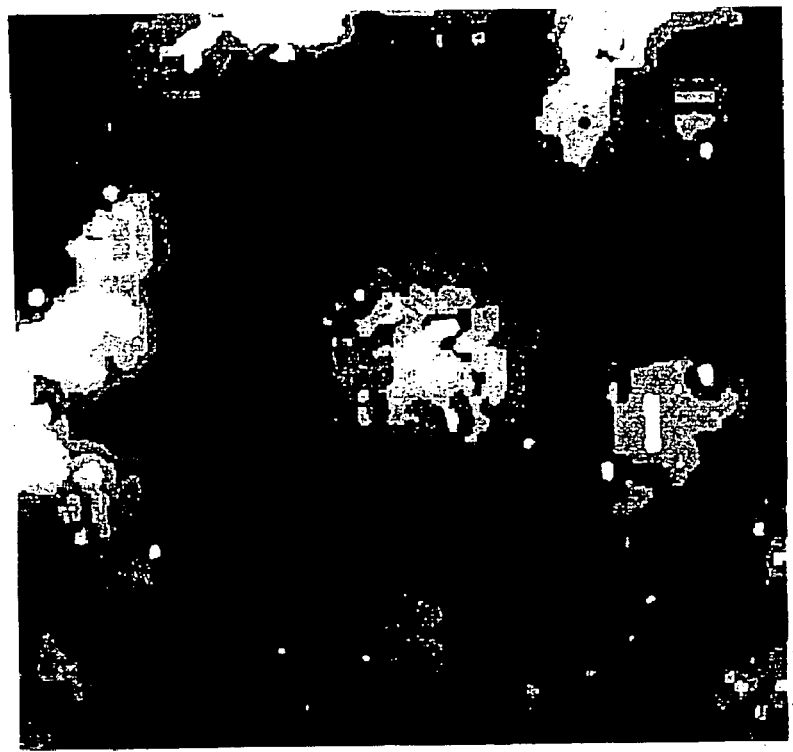
Figure 2I:
Figure 2H:
Figure 2J:
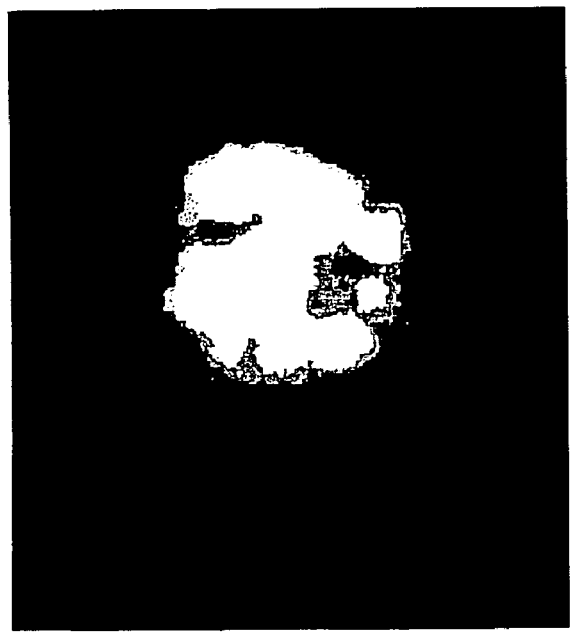
Figure 2K:
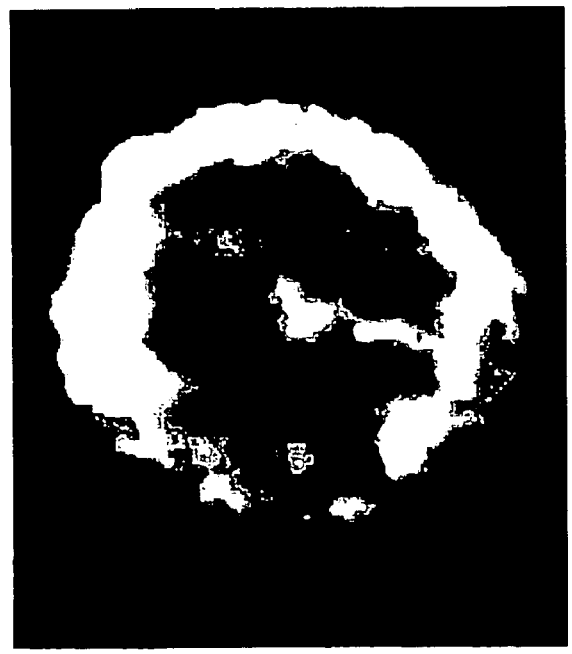
Figure 2L:
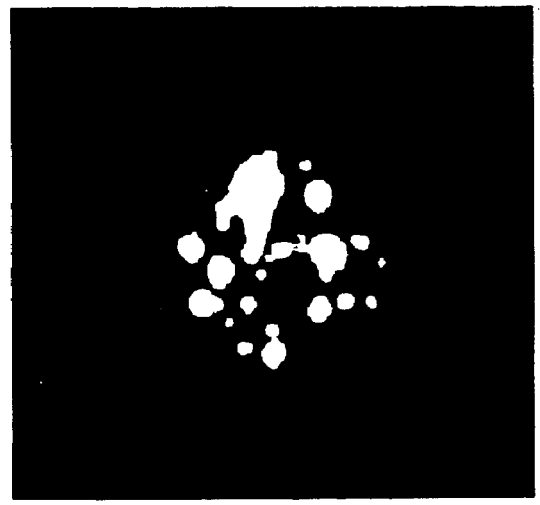
Figure 2M:
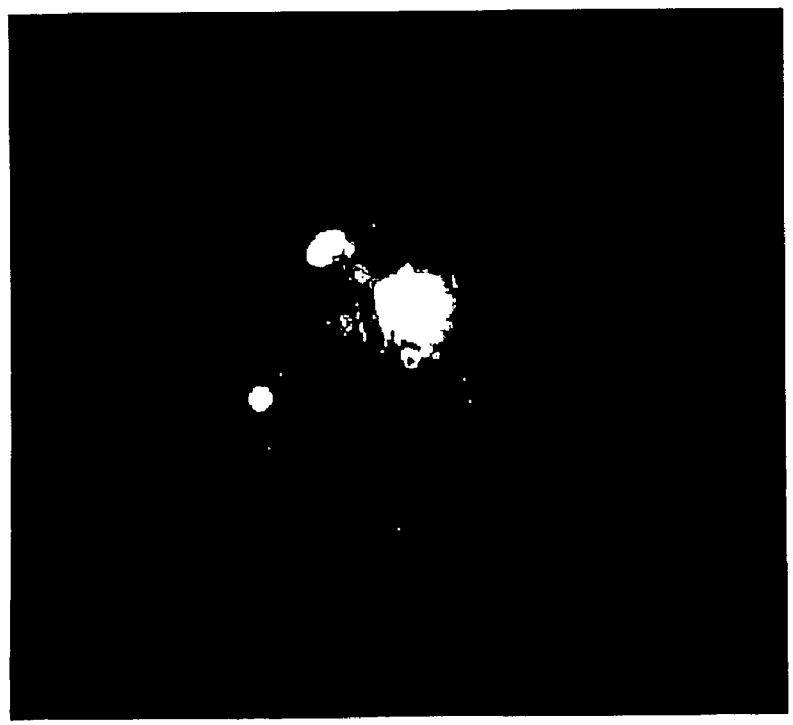
Figure 2N:
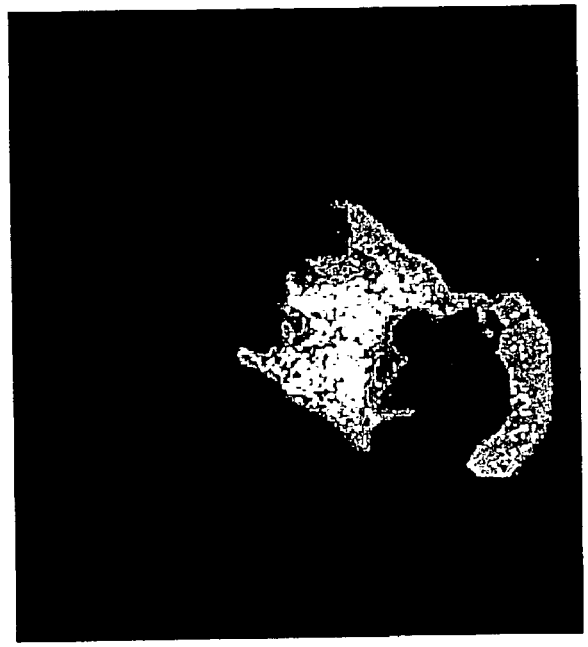
Figure 2O:
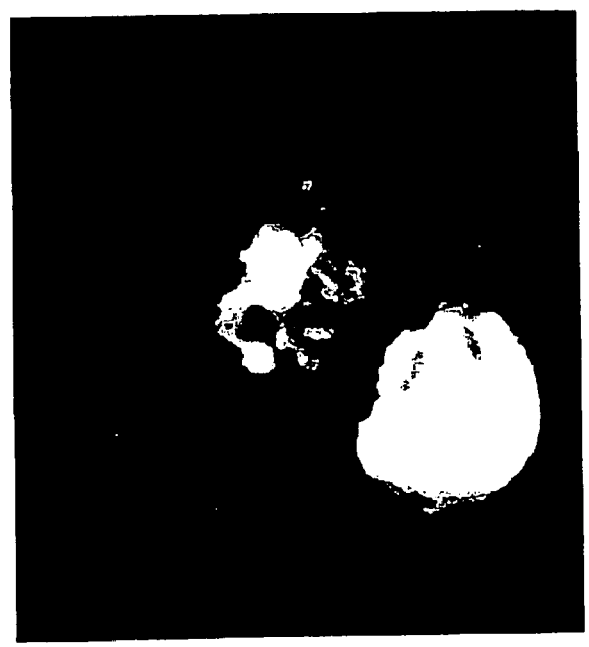
Figure 2P:
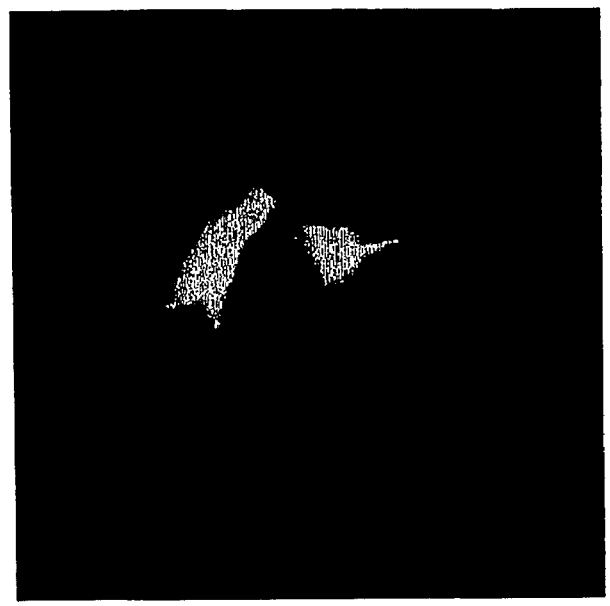
Figure 2Q:
Figure 2R:
Figure 2S:

Specifically, FIG. 2A depicts an image of cellular cytokeratin staining (CAM 5.2 labeled with FITC) of a stem cell-like cell (denoted as "A" in FIG. 1A). FIG. 2B depicts an image of the nucleus of a stem cell-like cell stained with DAPI. FIG. 2C depicts an image of cytokeratin staining of an indeterminate cell (denoted as "B" in FIG. 1B). FIG. 2D depicts an image of the nucleus of an indeterminate cell stained with DAPI, and FIG. 2E depicts an image of androgen gene staining of an indeterminate cell. FIG. 2F depicts an image of cellular cytokeratin staining of a terminal cell type (denoted as "C" in FIG. 1C). FIG. 2G depicts an image of the nucleus of a terminal "C" cell type stained with DAPI. FIG. 2H depicts chromosome 18 staining of a terminal "C" cell type. FIG. 2I depicts a monochrome image of cytokeratin staining of a terminal cell type (denoted as "D" in FIG. 1D). FIG. 2J depicts an image of the nucleus of a terminal cell type (denoted as "E" in FIG. 1E) stained with DAPI, and FIG. 2K depicts cell-specific PSMA staining of a terminal "C" prostate cell type. FIGS. 2L and 2M depict images of cytokeratin and nuclear staining of cellular fragments, respectively. FIGS. 2N, 2P, 2R and 2O, 2Q, and 2S depict images of cytokeratin (2N, 2P, and 2R) and nuclear (2O, 2Q, and 2S) staining of proliferative cells (denoted as "G." "H," and "I" in FIGS. 1G, 1H, and 1I).

A correlation of FIGS. 1A–1I and 2A–2S with cancer cell types isolated from cancer patients was conducted. Table 1 below illustrates the data compiled from eighteen advanced breast cancer patients.

TABLE 1

| Cell Type | Percentage of Cancer Cell Type |
|---|---|
| 1A (stem-cell like) | 0.0–0.5 |
| 1B (indeterminate) | 70.0–75.0 |
| 1G (dividing) | 0.01–0.1 |
| 1H & 1I (clusters & microtumors) | 5.0–10.0 |
| 1D (terminal) | 0.1–1.0 |
| 1E (terminal) | 5.0–10.0 |
| 1F (terminal) | 5.0–10.0 |

The majority of breast cancer cells (70 to 75%) are classified as the indeterminate cell type. 5.01 to 10.1% are designated as proliferative cells, and the terminal cell types comprise 10.1 to 21%. Similarly, prostate cancer cell studies suggest that the indeterminate and proliferative prostate cell types are roughly equivalent to characterized breast cancer cells.

EXAMPLE 3

Determination of Aneuploidy via DNA Quantification Method

This example illustrates a method to measure the nuclear DNA content in single cancer cells in comparison to white blood cells found within the same sample as a measure of aneuploidy. The fluorochrome, 4',6-diamidino-2-phenylindole (DAPI), binds to DNA with high specificity and the complex exhibits intense fluorescence (IFI—Integrated Fluorescent Intensity or # of pixels (area) multiplied by average fluorescence/pixel (density 1 µm)). This has permitted the measurement of DNA in nuclei and viral particles (Rao, JY et al, *Cancer Epidemiology, Biomarkers & Prevention*, 7: 1027–1033 (1998)), and in breast cancer cells (Coleman, AW, et al, *J. Histochem.& Cytochem.* 29: 959–968 (1981)).

The basis for the quantitative fluorescence image assay is a comparison of the DNA content of a reference cell, white blood cells (WBC) in this case, with the circulating epithelial cells (CEC) in question. Circulating WBCs are usually in the $G_0$ phase of the cell cycle and have 2 copies (2c) of DNA (=2N) content. Normal epithelial cells in $G_0$ to $G_1$ phase also have 2c DNA and at $G_2$-M phase have 4c DNA. Therefore, a ratio of the reference WBC DNA content to CEC DNA content greater than two if dividing and greater than one if not dividing is a specific measure of aneuploidy since a dividing cell with 3c or 4c DNA will have a 6c to 8c DNA content at $G_2$-M.

The assay is completely controlled internally since the nuclear DAPI fluorescence of the WBC and the cancer cell are compared on the same slide and measured within very close proximity on the slide. This eliminates any problems that may arise from staining, e.g., incubation time or DAPI concentration, or from image acquisition or image processing since the reference and test cells are always treated exactly alike.

Two prostate cancer cell lines (LnCap and TSU) and normal prostate cells (NPC) were spiked into blood and the samples were processed using standard protocols for cell isolation and cell staining (U.S. Pat. No. 5,962,237). Larger numbers of LnCap and TSU, as well as a third prostate cancer cell line (PC-3) were spiked into isolated WBCs and stained as above. The mounting medium contained DAPI (XHM003) at 0.5 µg/ml. Fluorescence images of DAPI-stained nuclei were acquired using exposure times of 0.5 to 3.0 seconds. Background images were acquired with a slide that contained DAPI mounting medium, but no cells. Prostate cells were identified by positive cytokeratin staining showing the presence of labeling.

DAPI fluorescence of WBC was linear with respect to exposure times of 0.5 to 3 seconds (for image acquisition) and DAPI concentration (0.5 to 1.5 µg/ml). The fluorescence per pixel should be below 2000 units per pixel to ensure linearity. For the blood-spiked samples, the ratio of LnCap nuclear DAPI fluorescence to WBC DAPI fluorescence ranged from 1.9 to 4.4 (16 cells) indicating that the cells in this cancer cell line were essentially all aneuploid (greater than 2N DNA). For TSU cells, the ratio ranged from 1.6 to 3.4 (13 cells) indicating that most (10 out of 13) had more than 2N DNA and were therefore aneuploid. These results are supported by previous FISH data, which showed that these two prostate cancer cell lines are aneuploid with respect to chromosome 18.

For NPC, cultured in the presence of mitogens, the NPC/WBC nuclear fluorescence ratios with respect to DAPI ranged from 1.0 to 1.5. Data from anti-Ki67-treated cells show that greater than 80% of NPC, grown in the presence of FBS, are in the growth phase of the cell cycle and should have NPC/WBC ratios greater than one.

When larger numbers of cancer cells were spiked into isolated WBCs, cytospun onto slides, and then analyzed to obtain the integrated fluorescence intensity of nuclear-bound DAPI, the data were as follows: LnCap-128 WBC and 56 cancer cells analyzed, 95% had greater than 2N content of DNA; TSU-89 WBC and 125 cancer cells analyzed, 90% had greater than 2N content of DNA; PC-3-95 WBC and 90 cancer cells analyzed, 94% had greater than 2N content of DNA.

In conclusion, the human karyotype is very tight, therefore aneuploidy is an excellent marker for identifying cancer cells. Any CEC whose CEC/WBC nuclear DAPI fluorescence ratio is greater than two (more than 4N content of DNA) should be considered neoplastic (see LnCap model). Over 95% of the cells in normal differentiated prostate tissue should be in $G_0/G_1$ phase of the cell cycle (=2N DNA). Therefore, the finding of any CEC of prostate origin in the peripheral blood should be suspect, especially if the cell has a CEC/WBC nuclear DAPI fluorescence ratio of 1.3 or greater. Such cells could be aneuploid since the majority of normal prostate cells would not have greater than 2N content of DNA, that is a CEC/WBC of approximately one.

TABLE 2

WBC versus Normal Prostate Cells (NPC)

| | | | | NPC | | |
|---|---|---|---|---|---|---|
| Image | WBC No. evaluated | WBC Mean IFI × 1000 | WBC Area Range IFI | IFI single NPC | DNA ratio (NPC IFI/mean WBC IFI) | Status* |
| 1 | 9 | 234 | 196–271 | 267 | 1.1 | ND |
| 2 | 11 | 274 | 209–344 | 344 | 1.3 | D |
| 3 | 11 | 328 | 282–377 | 478 | 1.5 | D |
| 4 | 9 | 270 | 209–317 | 363 | 1.3 | D |
| 5 | 11 | 218 | 184–233 | 346 298 | 1.6 | D |
| 6 | 12 | 268 | 213–330 | 419 | 1.4 | D |
| 7 | 10 | 324 | 297–353 | 313 | 1.0 | ND |
| 8 | 10 | 275 | 234–304 | 266 | 1.0 | ND |

*D = Dividing cells (ratio > 1.2), ND = Non-dividing cells (ration < 1.2)
**NPC = Prostate Epithelial Cell Line PrEC (Clonetics Cat. No. CC2655)

Average. WBC IFI for eight different images from the same slide is 274,000 with a standard deviation of 38,000.

Average WBC area, in pixels, for the eight different images ranged from 729 to 1019. Area of NPC ranged from 1159 pixels to 1651 pixels.

Table 3 illustrates the cancer cell/WBC DNA ratio of four types of cancer (breast, colon, gastric, and prostate). Cells were cultured as discussed above. In all cases, the data indicate that the majority of the cancer cells are aneuploidy, wherein the DNA ratio is greater than 2.0. For the cancer cells that do not show a ratio greater than 2.0, it may be that they are in the $G_0$–$G_1$ phase of the cell cycle.

TABLE 3

WBC versus Cancer Cell Lines

| | Breast MCF-7 | Breast T47D | Colon HT-29 | Gastric KATO III | Prostate LnCap | Prostate TSU |
|---|---|---|---|---|---|---|
| No. of cells analyzed | 55 | 45 | 31 | 25 | 16 | 13 |
| Median cancer cell/WBC ratio | 2.02 | 1.65 | 1.71 | 2.50 | 2.50 | 2.05 |
| Mean Cancer Cell/WBC ratio | 2.24 | 1.82 | 2.05 | 2.90 | 2.62 | 2.26 |
| Range of Cancer Cell/WBC Ratio | 1.5–3.5 | 1.2–3.5 | 1.4–3.7 | 1.8–4.9 | 1.9–4.4 | 1.6–3.4 |

EXAMPLE 4

Thymiylate Synthetase

This example illustrates the procedure for testing the expression of thymidylate synthetase in an enriched population of cancer cells.

Figure 4A:
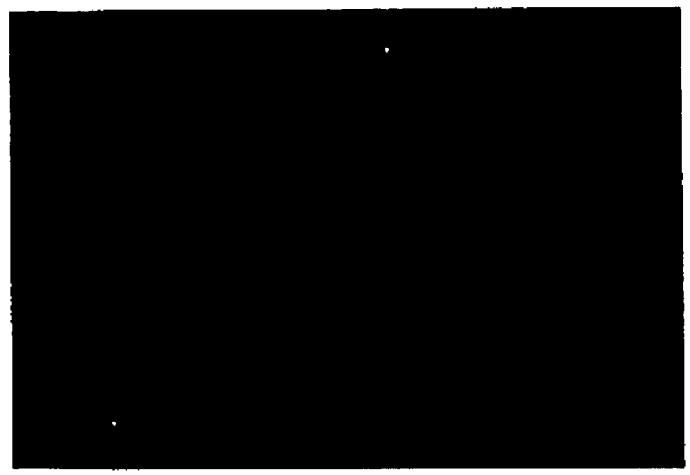
FIGS. 4A and 4B are monochromatic images of cells depicting TS antibody staining.
Figure 4B:
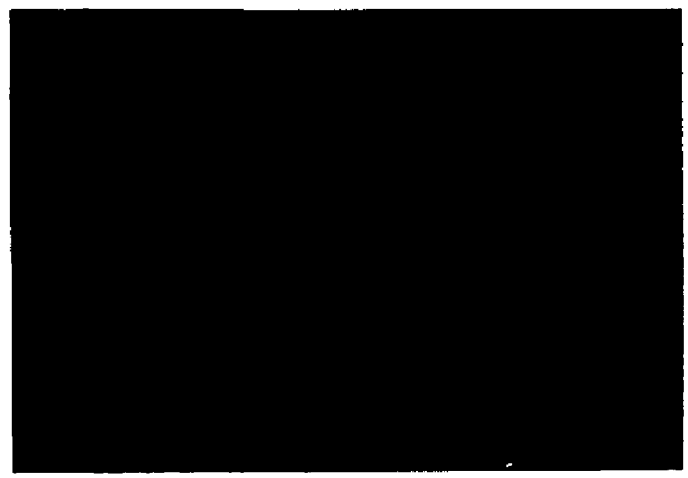

Cultured breast cancer cells were added into about 8.0 ml whole blood and mixed well and gently by inversion three times. The mixture was diluted to 35 ml with 1×PBS in a 50 ml polypropylene tube and mixed by inversion three times. Fifteen ml of 1.077 g/ml gradient were added to the bottom of the blood using a syringe with a long needle. The cells (WBC+breast cancer cells) were isolated from the red blood cells using 1.077 g/ml gradient at 1600 rpm centrifuge for 20 minutes. The cell pellets (~2 ml) were diluted with 1×PBS to 45 ml and re-collected after a 10 minute centrifugation at 1000 rpm. The pelleted cells were resuspended with 6 ml of 0.1% BSA (1×PBS+0.1% BSA), cytospun onto a slide using Cytofunnel at 500 rpm for 5 minutes. Cells were fixed on the slide at 2% paraformaldehyde for 10 minutes. The slide was washed two times (5 minutes×2) with 1×PBS. Next, 30 µl 5% milk in 1×PBS was added and incubated at RT for 10 minutes in a moisture box. The slides was washed once with 1×PBS, and 30 µl TS106 antibody (1:100 dilution with permeability buffer; Lab Vision, Fremont, Calif.) was added prior to incubation at RT for 1 hour. The slide was washed two times (5 minutes×2) with 1×PBS, and FITC labeled mouse anti-human antibody (I:100) was added prior to incubation at RT for 1 hour. The slide was washed two times (5 minutes×2) with 1×PBS, and 30 µl 1:50 diluted anti-cytokeratin antibody was added at RT for 30 minutes. The slide was washed two times (5 minutes×2) with 1×PBS and the slide was air-dried. Six µl of DAPI was added, the slides was covered with a glass cover, the expression of TS was determined under a microscope. FIGS. 4A and 4B show LnCap cells that were immunocytochemically stained by cytokeratin antibody and TS antibody.

EXAMPLE 5

Additional Markers

This example illustrates various other optional markers that are available for testing on cancer cells that may be isolated from body fluid samples. The following figures depict tested breast and prostate cell lines using the isolation and staining procedure outlined in Example 1.

Figure 5A:
FIGS. 5A and 5B are monochromatic images of cells depicting Her-2/neu antibody staining.
Figure 5B:
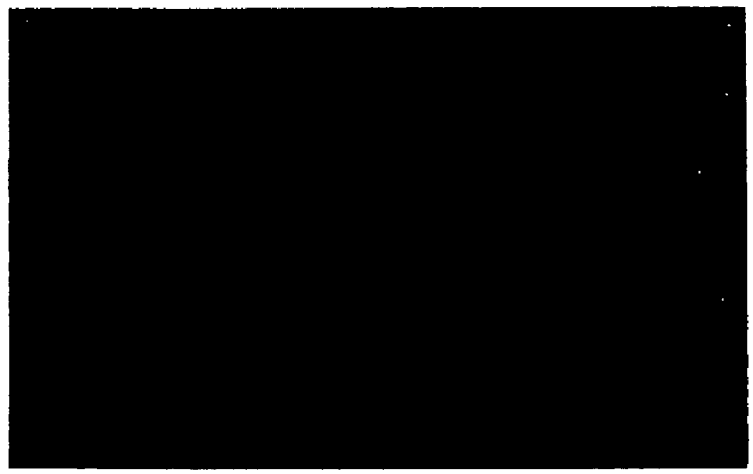

FIGS. 5A and 5B show cytokeratin and HER-2/neu antibody staining of LnCap cells.

Figure 6A:
FIGS. 6A and 6B are monochromatic images of cells depicting Bcl-2 antibody staining.
Figure 6B:

FIGS. 6A and 6B show LnCap cells that were immunocytochemically stained with an anti-cytokeratin antibody and a Bcl-2 antibody.

Figure 7A:
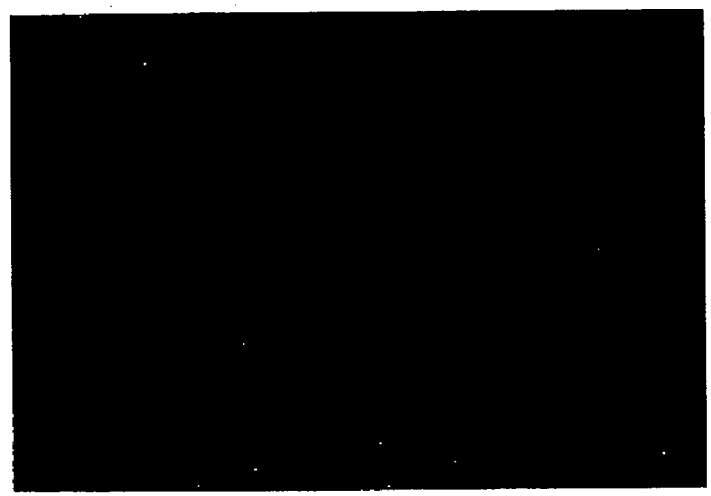
FIGS. 7A and 7B are monochromatic images of cells depicting p53 antibody staining.
Figure 7B:

FIGS. 7A and 7B show PC-3 prostate cells that were immunocytochemically stained with an anti-cytokeratin antibody and a p53 antibody.

Figure 8A:
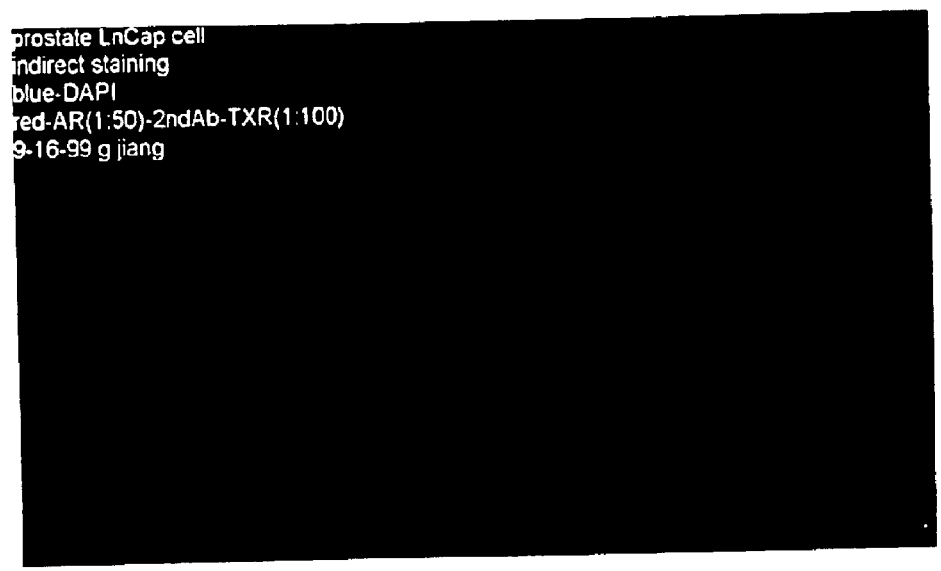
FIGS. 8A and 8B are monochromatic images of cells depicting androgen receptor antibody staining.
Figure 8B:
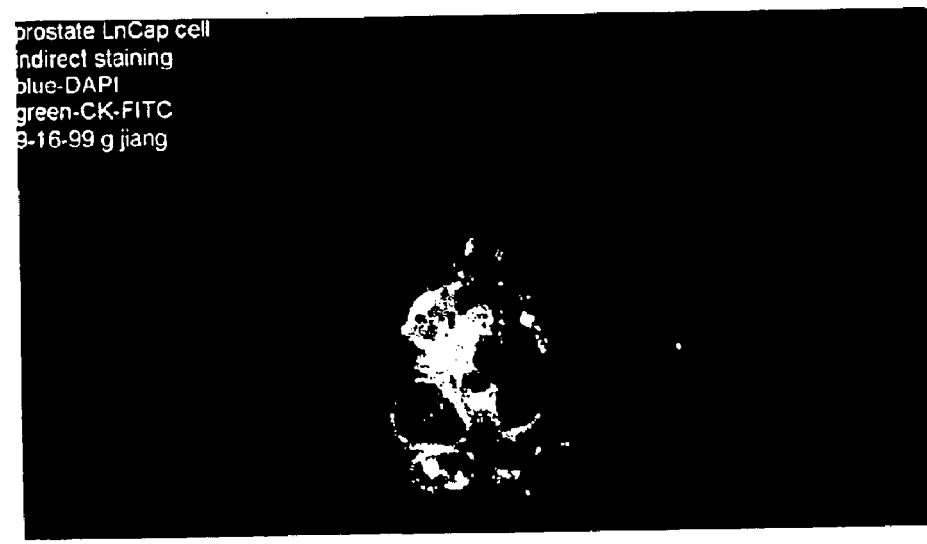

FIGS. 8A and 8B illustrate the detection of androgen receptor using androgen receptor antibody and androgen receptor gene copy mutation for LnCap prostate cancer cells. AR gene copies are multiplied in most of circulating cancer cells. FIGS. 8A and 8B also depict LnCap cells that were immunocytochemically stained with an anti-cytokeratin antibody.

FIGS. 9A, 9B, and 10 illustrate TUNEL staining for the detection of circulating cancer cell death. TUNEL staining measures nucleotide incorporation which may be used to discriminate apoptosis from necrosis. Cell line—breast cancer cell line MCF7 (ATCC NO. HTB-22).

Figure 11A:
FIGS. 11A and 11B depict monochromatic images of positive Ki67 (11A); and p27 (11B) staining of LnCap cells.
Figure 11B:
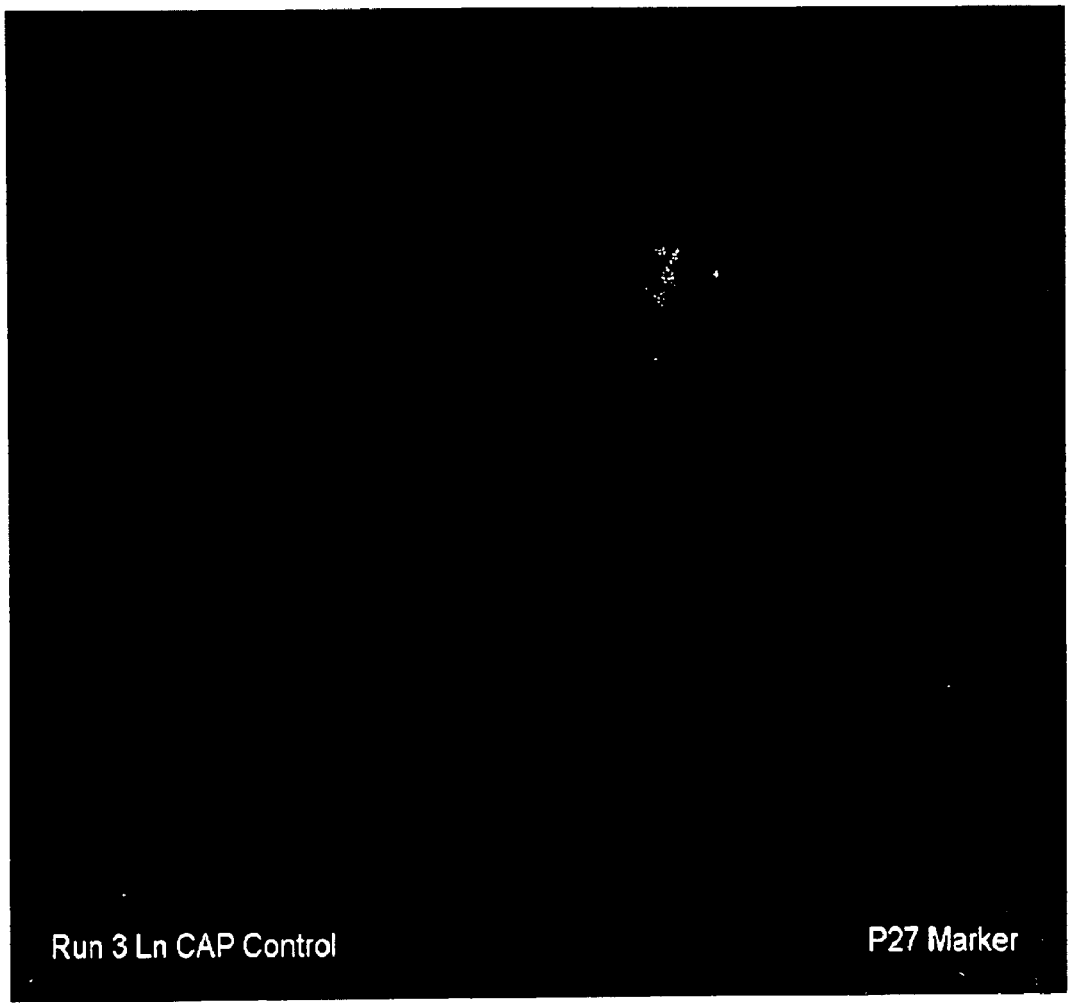
Figure 12A:
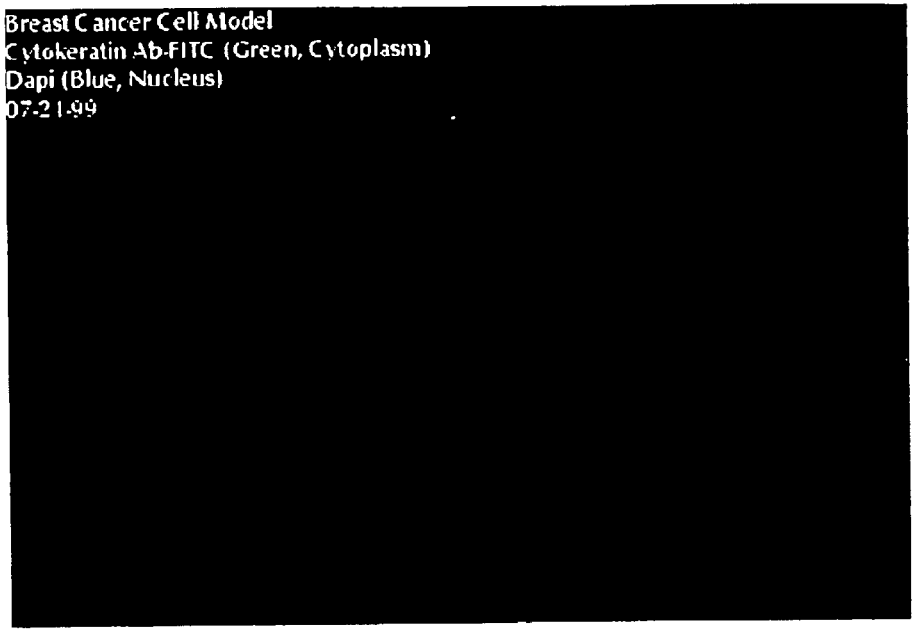
FIGS. 12A and 12B are monochromatic images of breast cancer cells with estrogen antibody staining.
Figure 12B:
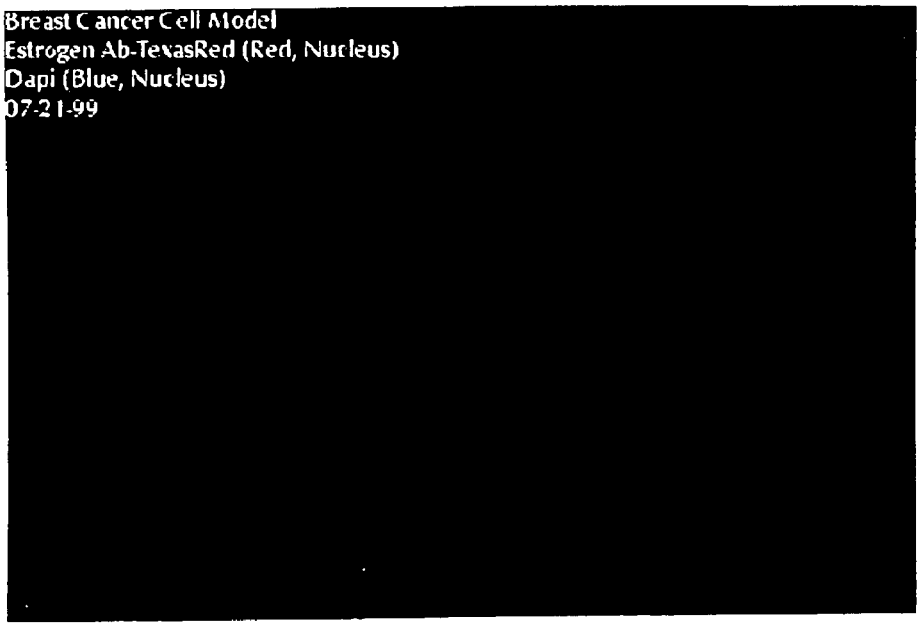
Figure 13A:
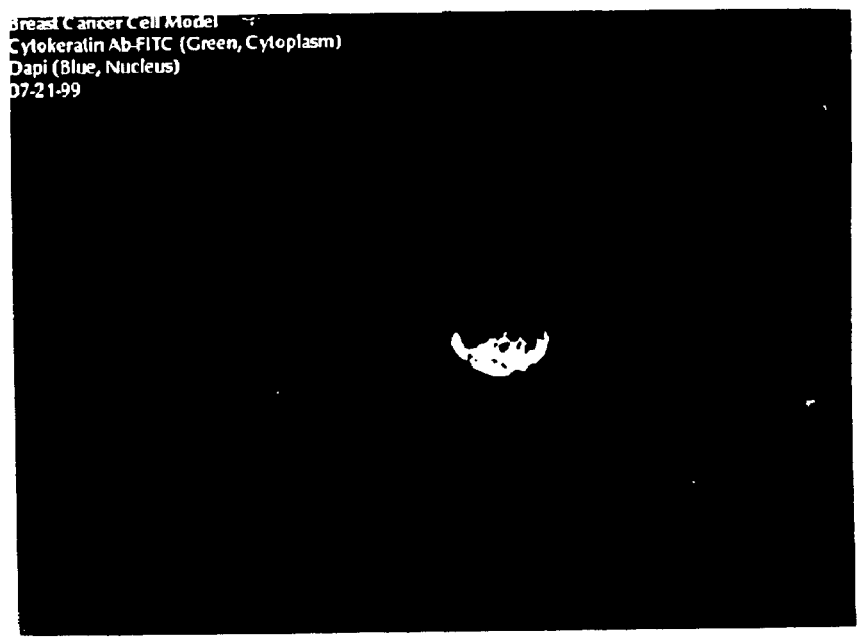
FIGS. 13A and 13B are monochromatic images of breast cancer cells with progesterone antibody staining.
Figure 13B:
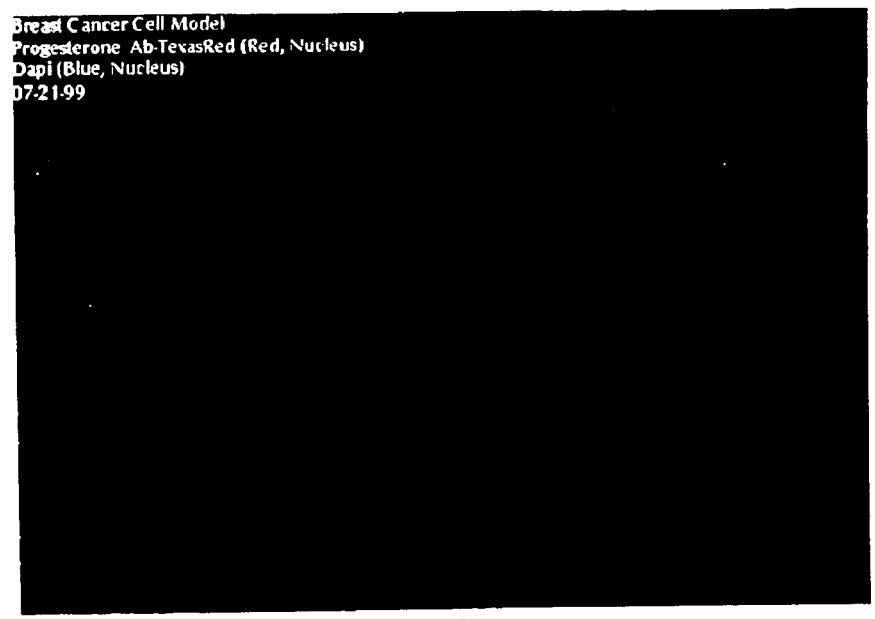

FIGS. 11A and 11B illustrate cytokeratin, p27, Ki67, DAP1 staining. An immunocytochemical staining technique and its semi-quantitative analysis of Ip27/Ki67 expression in the circulating cancer cells has been established. The cell line is the LnCap prostate cell line (ATCC No. CRL-1740).

FIGS. 12A and 12B and 13A and 13B illustrate estrogen (FIGS. 12A and 12B) (cell line MCF7 (ATCC No. HTB-22)) and progesterone (FIGS. 13A and 13B) (cell line T47D (ATCC No. HTB-133)) antibody staining in breast cancer cells.

The invention may be embodied in other specific forms without departing from the spirit or essential characteristics thereof. The present embodiments are therefore to be considered in all respects as illustrative and not restrictive. Patents, patent applications, and publications cited herein are hereby incorporated in their entireties by reference.

What is claimed is:

1. A method of classifying epithelial cancer cells in a sample of blood from a patient with cancer or a patient suspected of having cancer, said method comprising: isolating circulating epithelial cancer cells from said sample, and classifying said isolated cancer cells as terminal cells or proliferative cells by cytological and morphological analyses using fluorescence microscopy.

2. The method of claim 1, wherein at least one cancer cell is a terminal cell that is a fragile, large cancer cell compared to a white blood cell from the patient, and with a high nucleus to cytoplasm ratio when compared to a white blood cell from the patient.

3. The method of claim 2, wherein said terminal cell is about 20 micrometers to about 50 micrometers in diameter.

4. The method of claim 1, wherein at least one cancer cell is a terminal cell that is a fragile, large cancer cell compared to a white blood cell from the patient, and is without a nucleus.

5. The method of claim 4, wherein said terminal cell is about 20 micrometers to about 40 micrometers in diameter.

6. The method of claim 1, wherein at least one cancer cell is a terminal cell with a nucleus.

7. The method of claim 6, wherein said terminal cell is a late-stage dying cell and is breaking into pieces.

8. The method of claim 1, wherein at least one cancer cell is a proliferative cell.

9. The method of claim 8, wherein said cancer cell is about 25–35 micrometers in diameter.

10. The method of claim 8, wherein said cancer cell is a proliferative cell that is a dividing cell.

11. The method of claim 1, wherein three to 100 of said isolated cancer cells are in the form of a microtumor.

12. A method of determining the presence or absence of epithelial cancer cells capable of causing metastatic cancer, said method comprising:
   (a) isolating circulating epithelial cancer cells in a sample of blood from a patient with cancer or a patient suspected of having cancer; and
   (b) classifying said isolated cancer cells as terminal cells or proliferative cells by cytological and morphological analyses using fluorescence microscopy, thereby determining the presence or absence of cancer cells capable of causing metastatic cancer.

13. A method of determining the efficacy of a medical procedure for treatment of cancer in a patient, said method comprising:
   (a) conducting a first isolation of circulating epithelial cancer cells in a sample of blood from the patient;
   (b) classifying said isolated cancer cells as terminal cells or proliferative cells by cytological and morphological analyses using fluorescence microscopy;
   (c) conducting a second isolation of circulating epithelial cancer cells in a sample of blood from the patient;
   (d) repeating (b) on said second isolated cancer cells; and
   (e) comparing the number of said first isolated cancer cells to the number of said second isolated cancer cells, or comparing the classes of said first isolated cancer cells to the classes of said second isolated cancer cells, wherein the first isolation is conducted before the administration of the medical procedure and the second isolation is conducted after the administration of the medical procedure, thereby determining the efficacy of said medical procedure.

14. The method of claim 13, wherein the presence of more terminal cells in the second isolation than in the first isolation is indicative of a positive response to the medical procedure.

15. The method of claim 13, wherein the presence of more proliferative cells in the second isolation than in the first isolation is indicative of a negative response to the medical procedure.

16. The method of claim 13, wherein an increase or no change in the level of circulating cancer cells during or after terminating the medical procedure is indicative of a negative response to the medical procedure.

17. The method of claim 13, wherein said medical procedure is selected from the group consisting of surgery, radiation, hormone therapy, gene therapy, and therapeutic agent(s) administration, and a combination thereof.

18. The method of any one of claims 1, 12 and 13, wherein said cancer cells are breast cancer cells.

19. The method of any one of claims 1, 12 and 13, wherein said cancer cells are prostate cancer cells.

* * * * *